United States Patent
Kalayeh

(10) Patent No.: US 7,260,507 B2
(45) Date of Patent: Aug. 21, 2007

(54) METHOD FOR IMPROVING THE PERFORMANCE ACCURACY IN DIFFERENTIAL ABSORPTION LIDAR FOR OIL AND GAS PIPELINE LEAK DETECTION AND QUANTIFICATION

(75) Inventor: Hooshmand Mahmood Kalayeh, Pittsford, NY (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 11/223,241

(22) Filed: Sep. 9, 2005

(65) Prior Publication Data

US 2007/0061114 A1   Mar. 15, 2007

(51) Int. Cl.
   G06F 15/00   (2006.01)
(52) U.S. Cl. .................. 702/191; 702/69; 702/179; 356/432; 356/437; 73/335.01; 324/612; 324/614; 342/165; 250/338.1
(58) Field of Classification Search .............. 702/69, 702/179, 191; 356/432–437; 73/335.01; 324/612, 614; 342/165; 250/338.1

See application file for complete search history.

(56) References Cited

U.S. PATENT DOCUMENTS

| | | | |
|---|---|---|---|
| 4,450,356 A * | 5/1984 | Murray et al. | 250/339.11 |
| 6,509,566 B1 | 1/2003 | Wamsley et al. | |
| 6,822,742 B1 * | 11/2004 | Kalayeh et al. | 356/437 |
| 6,864,983 B2 * | 3/2005 | Galle et al. | 356/437 |
| 6,995,846 B2 * | 2/2006 | Kalayeh et al. | 356/437 |
| 2004/0088113 A1 | 5/2004 | Spoonhower et al. | |
| 2004/0263852 A1 | 12/2004 | Degtiarev et al. | |

FOREIGN PATENT DOCUMENTS

WO   WO 02/27297 A   4/2002

OTHER PUBLICATIONS

Hardesty et al., 'LIDAR Applications in Regional Air Quality Studies', 2000, IEEE Publications, pp. 1029-1031.*
Minren et al., 'The Antennas for the Propulsion Plume Attenuation Test', 2004, IEEE Publication, pp. 78-81.*
Peters et al., 'Rocket Plume Image Sequence Enhancement Using 3D Operators', Apr. 1997, IEEE Publication, vol. 33, No. 2, pp. 485-498.*

(Continued)

Primary Examiner—John Barlow
Assistant Examiner—Elias Desta
(74) Attorney, Agent, or Firm—RatnerPrestia

(57) ABSTRACT

An improved method for determining whether a measurement point, measured using a differential absorption LIDAR (DIAL) system, represents a plume point or a non-plume point. Concentration path lengths (CPL's) for a plurality of measurement points are determined. An average non-plume CPL, $\overline{CPL}$, is provided. For each measurement point, a standard deviation, $CPL_{sd}$, is calculated based on first order error propagation and it is determined that the measurement point represents a non-plume point when the Hooshmand decision rule (HDR) is met. The HDR is given by, $$\left(\frac{cpl - \overline{CPL}}{CPL_{sd}}\right)^2 > (T)^2,$$

where cpl is the corresponding CPL of the measurement point being tested and T is a threshold standard deviation level.

32 Claims, 9 Drawing Sheets

OTHER PUBLICATIONS

E. P. Mackerrow et al., "Effect of speckle on lidar pulse-pair ratio statistics", Applied Optics, vol. 36, No. 33, Nov. 20, 1997, pp. 8650-8669.

International Search Report Application No. PCT/US2006/032106 dated Dec. 15, 2006.

* cited by examiner

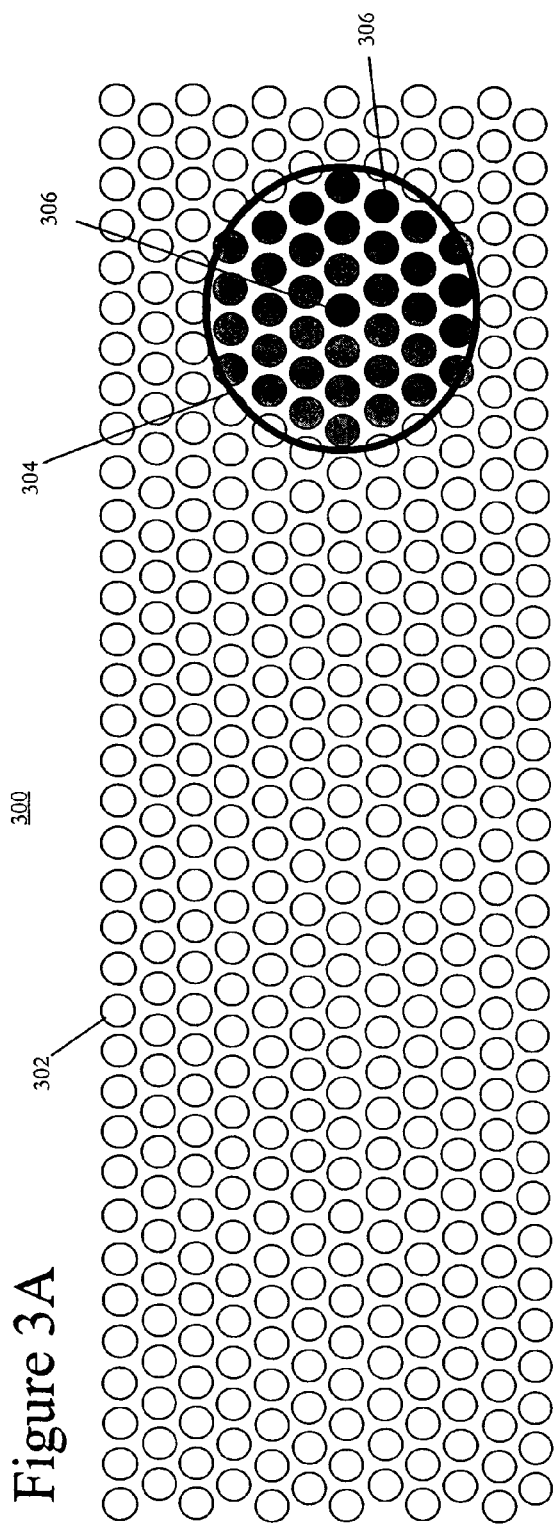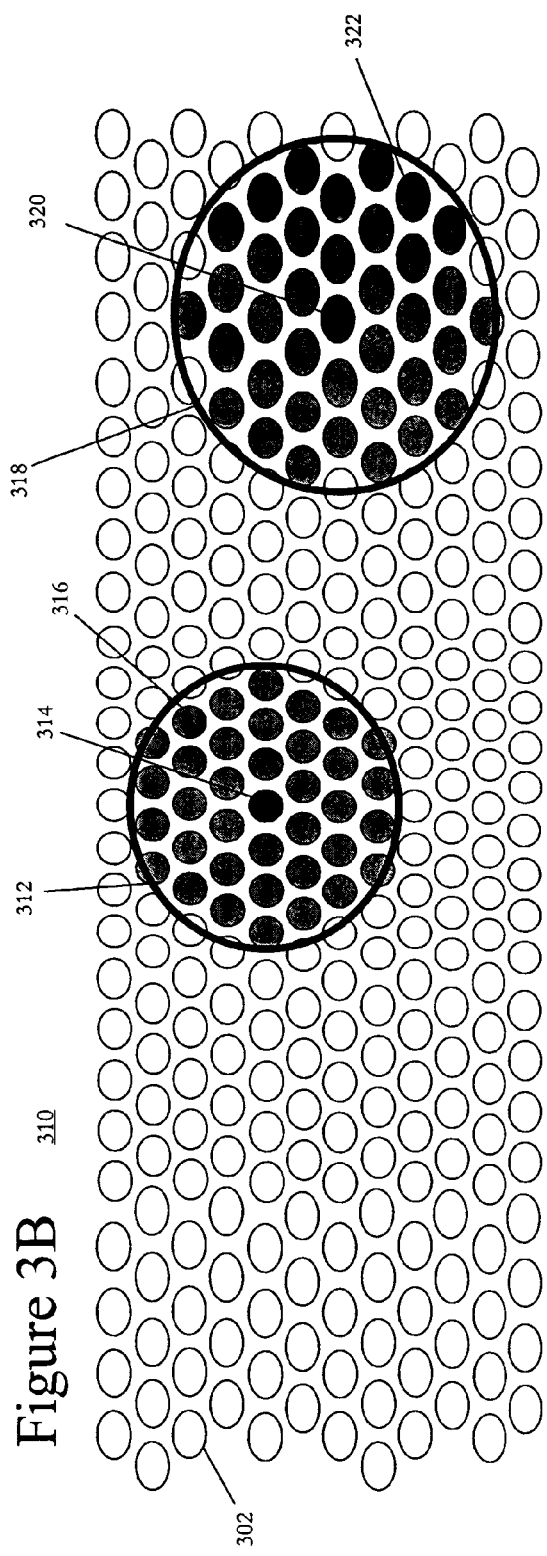
Figure 3A
Figure 3B

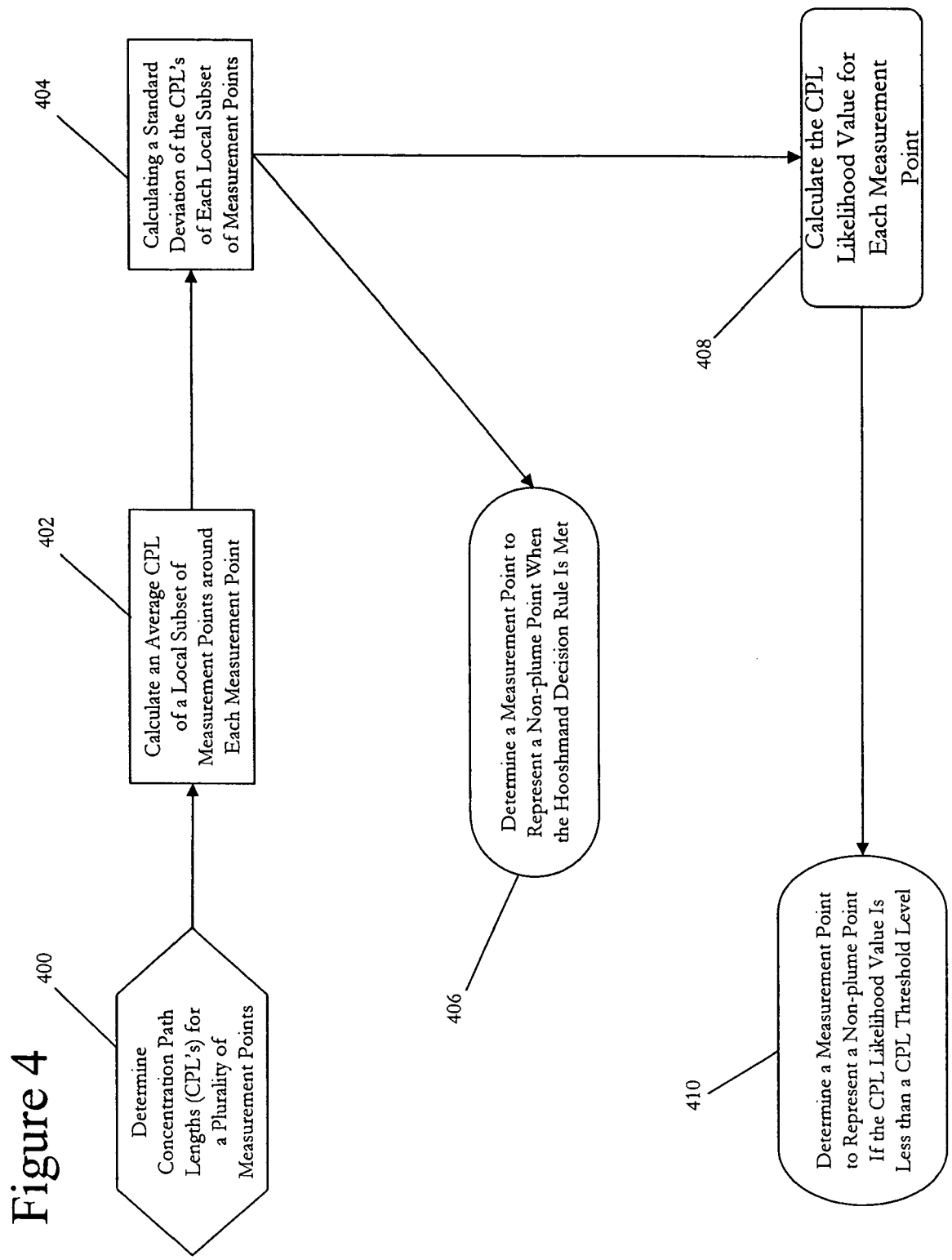

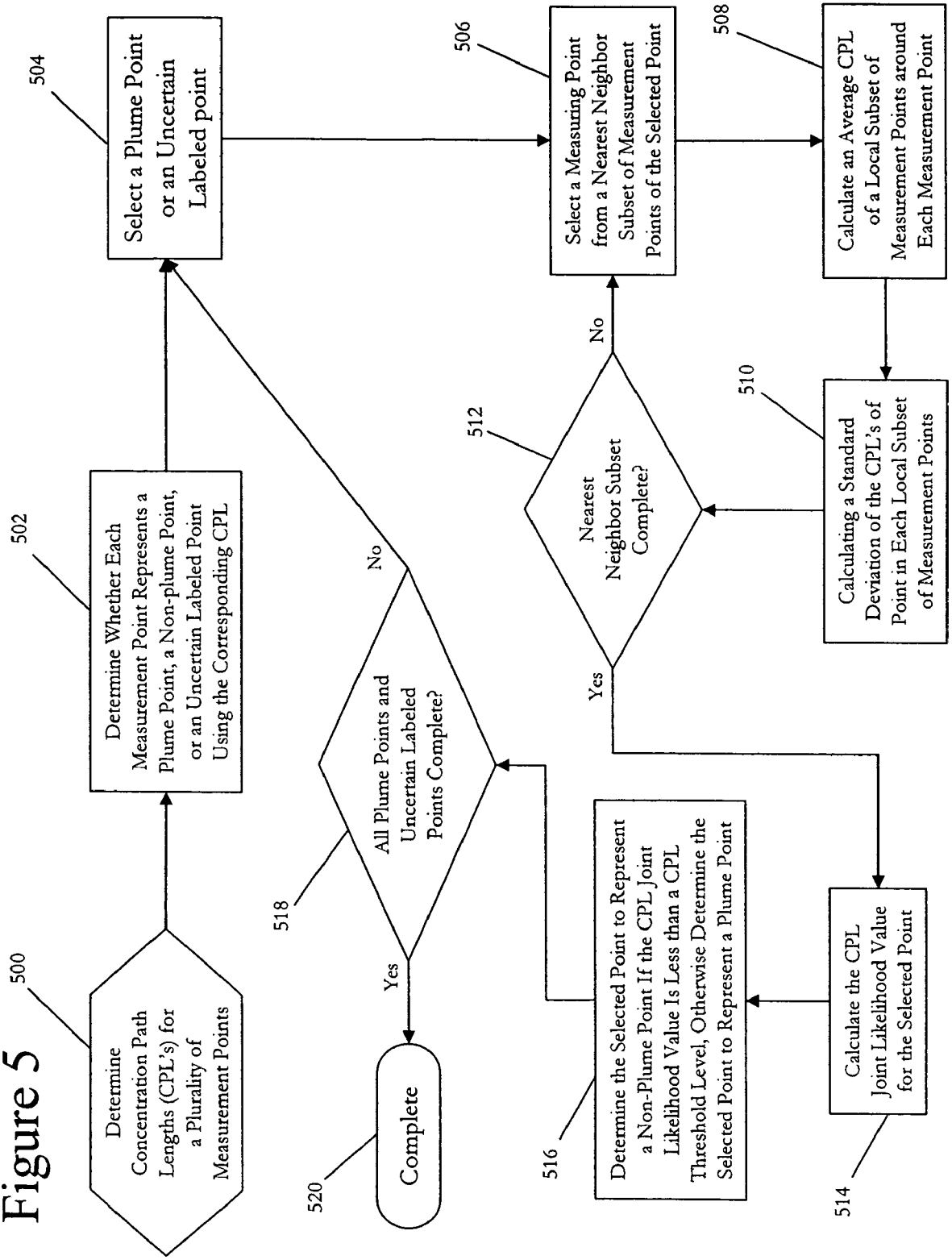

US 7,260,507 B2

METHOD FOR IMPROVING THE PERFORMANCE ACCURACY IN DIFFERENTIAL ABSORPTION LIDAR FOR OIL AND GAS PIPELINE LEAK DETECTION AND QUANTIFICATION

FIELD OF THE INVENTION

The present invention concerns a method for improving the accuracy of identifying plumes containing a target molecule using a differential absorption LIDAR (DIAL) system. In particular, this method may allow for improved signal to noise ratios for detection of plumes.

BACKGROUND OF THE INVENTION

In a DIAL system, the received back scattered signal is a function of: the transmitted laser pulse energy; the speed of light; the laser pulse width; the telescope area (field of view); the range (inverse square law); the offline beam and online beam overlap and the field of view (i.e. the geometric form factor); the spectral response of the receiver optics; the plume transmission; the total atmospheric transmission; and the ground cover type.

One use of a two-line DIAL system is to estimate the concentration path length (CPL) of a fluid related plume. Therefore, the online wavelength is desirably selected such that it is only absorbed by the target molecule of the fluid and nothing else in the optical path. The offline wavelength is desirably selected such that it is not absorbed by the target molecule or any other anticipated molecules allow the optical path. More desirably, the online and offline wavelengths are selected such that the ratio of the geometric form factor, the spectral response of the receiver optics, and the surface reflectivity corresponding to the online and offline wavelengths are approximately the same. As may be seen in Equation 1, when this condition is met, these parameters may cancel out, simplifying calculation of the CPL.

$$CPL = \frac{\ln\left(\frac{E(\lambda_{Off}, R)E_1(\lambda_{On})\xi(R_{On})\xi(\lambda_{On})\rho(\lambda_{On})}{E(\lambda_{On}, R)E_1(\lambda_{Off})\xi(R_{Off})\xi(\lambda_{Off})\rho(\lambda_{Off})}\right) - 2\int_0^2 (k(\lambda_{On}, r) - k(\lambda_{Off}, r))dr}{2(\sigma(\lambda_{On}) - \sigma(\lambda_{Off}))} - RC_{t\text{-}bag},$$

Eq. (1)

where $\lambda_{On/Off}$ is the online (or offline) peak wavelength, $\sigma(\lambda_{On/Off})$ is the online (or offline) cross-section, $E_1(\lambda_{On/Off})$ is the online (or offline) transmitted laser pulse energy, R is the range/altitude/distance of the sensor to the target, $E(\lambda_{On/Off}, R)$ is the online (or offline) received laser pulse energy, $\xi(R_{On/Off})$ is the geometric form factor for the online (or offline) peak wavelength, $\xi(\lambda_{On/Off})$ is the spectral response of the receiver optics for the online (or offline) peak wavelength, $\rho(\lambda_{On/Off})$ is the background surface reflectance for the online (or offline) peak wavelength, $k(\lambda_{On/Off}, r)$ is the atmospheric attenuation coefficient for the online (or offline) peak wavelength, and $C_{t\text{-}bag}$ is the target molecule concentration in the atmosphere.

In many cases, the dominating factor in DIAL system performance is the low signal relative to noise, or low Signal to Noise Ratio (SNR), and not electrical noise in the system. This problem may be especially acute when the SNR varies. In such situations the DIAL equation must be corrected to account for non-uniform variations and error (bias). The main source of these errors or non-uniform variations of the online and offline retuned signals are surface cover type spectral reflectivity variations and/or the misalignment of the online and offline beams (partially-overlapping beams). Partially overlapped beams may also lead to surface spectral reflectivity variations in the online and offline retuned signals. The online and offline wavelength desirably do not vary during the operation of the DAIL system. Therefore, the wavelengths are typically electronically locked at preselected wavelengths. However, in practice, these wavelengths may slightly vary and these variations may lead to spikes in cross-section and other undesirable interfering absorption effects. Furthermore, the estimation of the probability density function of plume points associated with a gas leak may not be practical.

Low surface cover type reflectivity applications result in low return online and offline signals and high surface cover type reflectivity applications result in high return is online and offline signals. When the returned signal is low relative to noise then the electrical noise dominates and this leads to low Signal to Noise Ration (SNR) and large Concentration Path Length (CPL) Variance, but the opposite is also true. When the returned signals are high relative to noise then the signal dominates and this leads to high SNR and low CPL Variance. Therefore, since the surface reflectivity varies from point to point and from region to region, so do the retuned signals and SNR.

However, in practice DIAL systems may be calibrated accordingly. Unfortunately, correcting for reflectivity variations due to ground surface cover type may be difficult in many situations. If these ground surface cover type reflectivity variations are not properly corrected, significant errors in CPL estimates of the target molecule may result, leading to false identification of plumes (or lack of plumes).

The present invention involves a method for improving the performance accuracy in DIAL by utilizing spectral and spatial information. Improved methods of the present invention may increase (probability) certainty of detection of plumes containing the target molecule. For example, these improved methods may be useful in identification of plumes generated by leaks in pipelines or storage tanks, plumes caused by spills and other contamination, and naturally occurring plumes such as gases emitted by volcanoes.

SUMMARY OF THE INVENTION

An exemplary embodiment of the present invention is a method for improving the signal to noise ratio in a differential absorption LIDAR (DIAL) system. A DIAL beam is scanned such that the DIAL beam is transmitted through a plurality of measurement points. The DIAL beam includes an online laser beam and an offline laser beam that are transmitted substantially collinearly. A plurality of transmitted pulse energies of the online laser beam and a plurality of transmitted pulse energies of the offline laser beam corresponding to the plurality of measurement points are measured, as are a plurality of received pulse energies of the online laser beam and a plurality of received pulse energies of the offline laser beam corresponding to the plurality of measurement points. One measurement point is selected. A region of interest (ROI) subset of measurement points within a ROI around the one selected measurement point is selected as well. For the one selected measurement point a number of averages are calculated, including: an average transmitted online pulse energy from the transmitted pulse energies of the online laser beam of the selected ROI subset of the measurement points; an average transmitted offline pulse energy from the transmitted pulse energies of the offline laser beam of the selected ROI subset of the measurement points; an average received online pulse energy from the received pulse energies of the online laser beam of the selected ROI subset of the measurement points; and an average received offline pulse energy from the received pulse energies of the offline laser beam of the selected ROI subset of the measurement points. A concentration path length (CPL) of the DIAL beam for the one selected measurement point is calculated using the average transmitted online pulse energy, the average transmitted offline pulse energy, the average received online pulse energy, and the average received offline pulse energy.

An additional exemplary embodiment of the present invention is an improved method for determining whether a measurement point, measured using a differential absorption LIDAR (DIAL) system, represents a plume point or a non-plume point. Concentration path lengths (CPL's) for a plurality of measurement points are determined. An average non-plume CPL, $\overline{CPL}$, is provided. For each measurement point, a standard deviation, $CPL_{sd}$, is calculated based on first order error propagation. For each measurement point, the CPL likelihood value is calculated, $$CLL\_LL = -\frac{1}{2}\ln(2\Pi) - \ln(CPL_{sd}) - \frac{1}{2}\left(\frac{cpl - \overline{CPL}}{CPL_{sd}}\right)^2,$$

where cpl is the corresponding CPL of the measurement point. For each measurement point, it is determined that the measurement point represents a non-plume point if the CPL likelihood value is less than a CPL threshold level, $$CPL\_LL_{threshold} = -\frac{1}{2}\ln(2\Pi) - \ln(CPL_{sd}) - \frac{1}{2}(T)^2,$$

where T is a threshold standard deviation level.

Another exemplary embodiment of the present invention is an improved method for determining whether a measurement point, measured using a differential absorption LIDAR (DIAL) system, represents a plume point or a non-plume point. Concentration path lengths (CPL's) for a plurality of measurement points are determined. An average non-plume CPL, $\overline{CPL}$, is provided. For each measurement point, a standard deviation, $CPL_{sd}$, is calculated based on first order error propagation and it is determined that the measurement point represents a non-plume point when the Hooshmand decision rule (HDR) is met. The HDR is given by, $$\left(\frac{cpl - \overline{CPL}}{CPL_{sd}}\right)^2 > (T)^2,$$

where cpl is the corresponding CPL of the measurement point being tested and T is a threshold standard deviation level.

A further exemplary embodiment of the present invention is an improved method for discovering false plume points identified using a differential absorption LIDAR (DIAL) system. A concentration path length (CPL) for a plurality of measurement points is determined. For each measurement point, whether the measurement point represents a plume point or a non-plume point is determined using the corresponding CPL. A $j^{th}$ measuring point from a nearest neighbor subset of the measurement points of one of the plume points is selected. The nearest neighbor subset of the measurement points includes the plume point and a predetermined number, K-1, of nearest neighbor measurement points. An average CPL, $\overline{CPL_j}$, of the CPL's of a local subset of measurement points around the $j^{th}$ measurement point is calculated. A standard deviation, $(CPL_{sd})_j$, of each measurement point in the local subset is calculated based on first order error propagation. These calculations are carried out for j=1 to K. The CPL likelihood value of the one plume point is calculated, $$(CPL\_LL) = -\sum_{j=1}^{K}\ln(CPL_{sd})_j - \frac{1}{2}\sum_{j=1}^{K}\left[\frac{cpl_j - \overline{CPL_j}}{(CPL_{sd})_j}\right]^2,$$

where $cpl_j$ is the corresponding CPL of the $j^{th}$ measurement point. If the CPL likelihood value of the one plume point is less than a CPL threshold level of the one plume point, $$(CPL\_LL)_{Threshold} = -\sum_{j=1}^{K}\ln(CPL_{sd})_j - \frac{1}{2}KT^2,$$

where T is a threshold standard deviation level, then it is determined that the one plume point represents a false plume point. The process is repeated for each plume point.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawing are the following figures:

FIG. 3A is a schematic diagram illustrating an exemplary region of interest subset of measurement points for uniformly distributed measurement points of an exemplary linear scan pattern according to the present invention.

FIG. 3B is a schematic diagram illustrating two exemplary region of interest subsets of measurement points for variably distributed measurement points of another exemplary linear scan pattern according to the present invention.

FIG. 4 is a flow chart illustrating two alternative exemplary methods of determining whether a measurement point represents a plume or a non-plume point according to the present invention.

FIG. 5 is a flow chart illustrating an exemplary method of identifying false plume points according to the present invention.

DETAILED DESCRIPTION OF THE INVENTION

Exemplary embodiments of the present invention utilize spectral probability density and spatial joint probability density of the concentration path length (CPL) of local non-plume points, in a Differential Absorption LIDAR (DIAL) laser remote sensing system, to optimally detect and quantify the CPL of plume-points associated with a gas leaks. The local non-plume distribution parameters (mean and variance) are adaptively estimated. The CPL_MEAN is estimated based on the local non-plume computed CPL and CPL_VARIANCE is adaptively estimated for each return SNR.

Figure 1:
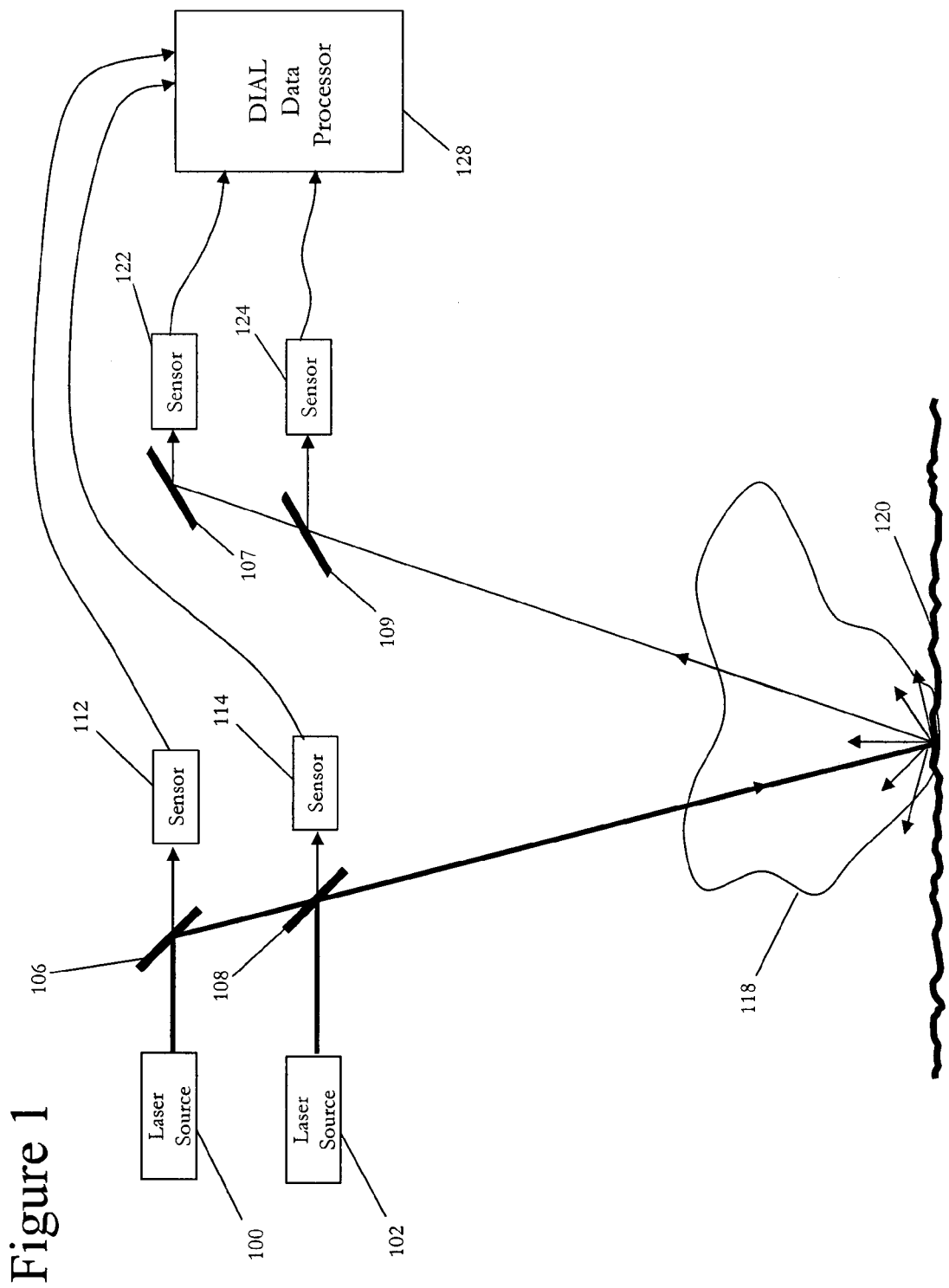
FIG. 1 is a schematic block diagram illustrating an exemplary differential absorption LIDAR (DIAL) system according to the present invention.

An exemplary embodiment of the present invention is an exemplary DIAL system, as illustrated in FIG. 1. This exemplary system includes two pulsed laser sources, online pulsed laser source 100 and offline pulsed laser source 102 to generate the DIAL beam. It is noted that the selection of one online pulsed laser source and one offline pulsed laser source in the exemplary embodiment of FIG. 1 is to simplify illustration and is not intended to be limiting. The discussion of exemplary DIAL systems below primarily focuses on the exemplary embodiment of FIG. 1, but it is contemplated that one skilled in the art may understand that additional offline pulsed laser sources may be included in an exemplary DIAL system according to the present invention.

Online pulsed laser source 100 generates an online laser beam that that includes a series of laser pulses. These pulses of the online laser beam have an online peak wavelength, $\lambda_{On}$, that is within an optical absorption band of the target molecule. Thus, the concentration path length of the target molecule within a measurement point may be determined using the resulting attenuation of the pulse energy of the online laser beam as the laser pulses propagate through the measurement point.

The transmitted pulse energy of the online laser beam, $E_1(\lambda_{On})$, may desirably be determined from a small portion of each pulse directed to optical sensor 112. This optical sensor forms part of an array of optical sensors that also includes optical sensor 114 which may be used to detect the transmitted pulse energies of the online and offline laser beams. The small portion of the online laser beam detected by optical sensor 112 may be separated using beam splitter 106, as shown in FIG. 1.

Offline pulsed laser source 102 generates an offline laser beam of laser pulses having an offline peak wavelength, $\lambda_{Off}$. This offline peak wavelength is selected to be outside of the optical absorption band of the target molecule so that the pulse energy of the offline laser pulse is not significantly affected by existence, or non-existence, of the target molecule along the beam path of the offline laser beam through the measurement point.

As with the online laser beam, the transmitted pulse energy of the offline laser beam, $E_1(\lambda_{Off})$, may desirably be determined from a small portion of each pulse directed to optical sensors 114. The small portion of the offline laser beam may be separated using dichroic beam splitter 108, which desirably reflects substantially all light with a wavelength $\lambda_{Off}$ and transmits substantially all light with a wavelength $\lambda_{On}$, as shown in FIG. 1.

The array of optical sensors 112 and 114 are coupled to provide signals proportional to the transmitted pulse energies of the two laser beams to DIAL data processor 128 for use in calculating the CPL of the target molecule at the measurement point.

Beam splitter 106 and dichroic mirror 108 may also operate as transmission optics to align the online laser beam and the offline laser beam such that the laser beams may be transmitted substantially collinearly to a series of measurement points on surface 120. In this way, the online laser beam and each of the offline laser beams may sample approximately the same beam path to each measurement point. Such similar beam paths are desirable to reduce any differences in the conditions experienced by the laser beams, other than those caused by the different wavelengths of the two laser beams, e.g. absorption of online laser beam by target molecules in plume 118. Also, the similarity of the beam paths is desirable so that the laser beams may both be reflected off of substantially the measurement point of inhomogeneous surface 120.

Although the exemplary embodiment of FIG. 1 is shown with beam splitter 106 and dichroic mirror 108 act both to separate the portions of each beam to be monitored by the array of optical sensors 112 and 114 and to align the laser beams substantially collinearly, it is contemplated that additional optical components, such as mirrors, gratings, and lens, may be included as well to accomplish these tasks. It is noted that it may also be desirable for the two laser beams to be substantially collimated to reduce spreading of the beams along the beam path from the exemplary DIAL system to inhomogeneous surface 120 and back. Additional optics and/or mechanical stages (not shown) may be included to allow scanning of the DIAL beam through a series of measurement point on surface 120 as well.

In many practical applications, inhomogeneous surface 120 may be a section of ground, which may have a variety of different forms of cover arranged over it, e.g. shrubs, trees, grass, pavement, etc. As shown in FIG. 1, inhomogeneous surface 120 and the various cover on it may appear rough. Thus, much of the pulse energy of each of the laser beams may be scattered and only a small amount of each pulse may make it back to the DIAL system to be measured.

The reduced optical signal caused by reflecting (scattering) the laser beams off of a rough surface may adversely effect sensitivity of CPL detection by reducing the signal to noise ratio of the exemplary DIAL system. Further, the variations in ground cover may lead to differences in the reflectivity of inhomogeneous surface 120 from one measurement position to another.

The exemplary embodiment of FIG. 1 includes a second set of optics, dichroic mirror 109 and mirror 107, to collect, separate by peak wavelength, and direct the reflected portions of the offline laser beam and the online laser beam received by the exemplary DIAL system to a second array of optical sensors 122 and 124. Desirably, dichroic mirror 109 may have similar properties to dichroic mirror 108. It is noted that this second set of receiver optics may include additional optical elements (not shown) as described above for the set of transmission optics.

The second array of optical sensors 122 and 124 sense the received pulse energies of the reflected portion of the online laser beam, $E(\lambda_{On},R)$ and the offline laser beam, $E(\lambda_{Off},R)$, respectively. This array of optical sensors is coupled to DIAL data processor 128 to provide signals proportional to the transmitted pulse energies of the laser beams to DIAL data processor 128 for use in calculating the concentration path length (CPL) of the target molecule.

DIAL data processor 128 uses the transmitted online and offline pulse energy signals from optical sensors 112 and 114 and the received online and offline pulse energy signals from optical sensors 122 and 124 measured at a number of different measurement points to determine a set of average transmitted online and offline pulse energies and received online and offline pulse energies associated with each measurement point. Desirably, these pulse energy values of each measurement point may be calibrated using known reflection and transmission coefficients of mirrors 112 and 122 and dichroic mirrors 108 and 109, as well as known conversion factors for optical sensors 112, 114, 122, and 124.

The DIAL data processor may then calculate the CPL for each measurement point using the corresponding average pulse energies. This calculation may be performed using Equation 1.

DIAL data processor may include one or more of: special purpose circuitry; an application specific integrated circuit (ASIC); or a general purpose computer programmed. Each of these potential elements may be used to perform at least one of the determining, estimating and calculating functions of the DIAL data processor.

A typical use of a DIAL system may be to identify plumes that include a target molecule resulting from a leak or spill of a pipeline or storage tank or from a natural source such as a volcano or geothermal vent. In addition to low SNR other factors may affect the ability of a DIAL system to distinguish plume versus non-plume points. For example, the CPL spatial distribution of a leak plume may be a function of leak size, roughness of leak nearest region, time, temperature and wind speed.

The measured size of a plume is the intersection of the plume with the beam path of the DIAL beam. A perfect plume in air looks like a flame candle form and the CPL of the center is higher than the surrounding plume area (spatially normally distributed). The plume size is related to the leak rate. In a still atmosphere, the closer a region is to the leak is the higher the CPL and the closer the measurement point is to the center of the plume the higher the CPL, but if there is significant air or water movement, the plume may be dancing around and, thus difficult to pinpoint. Thus, characterizing the spatial distribution of different plumes may prove difficult, leading to a desire for increased accuracy in CPL determination.

Figure 6:
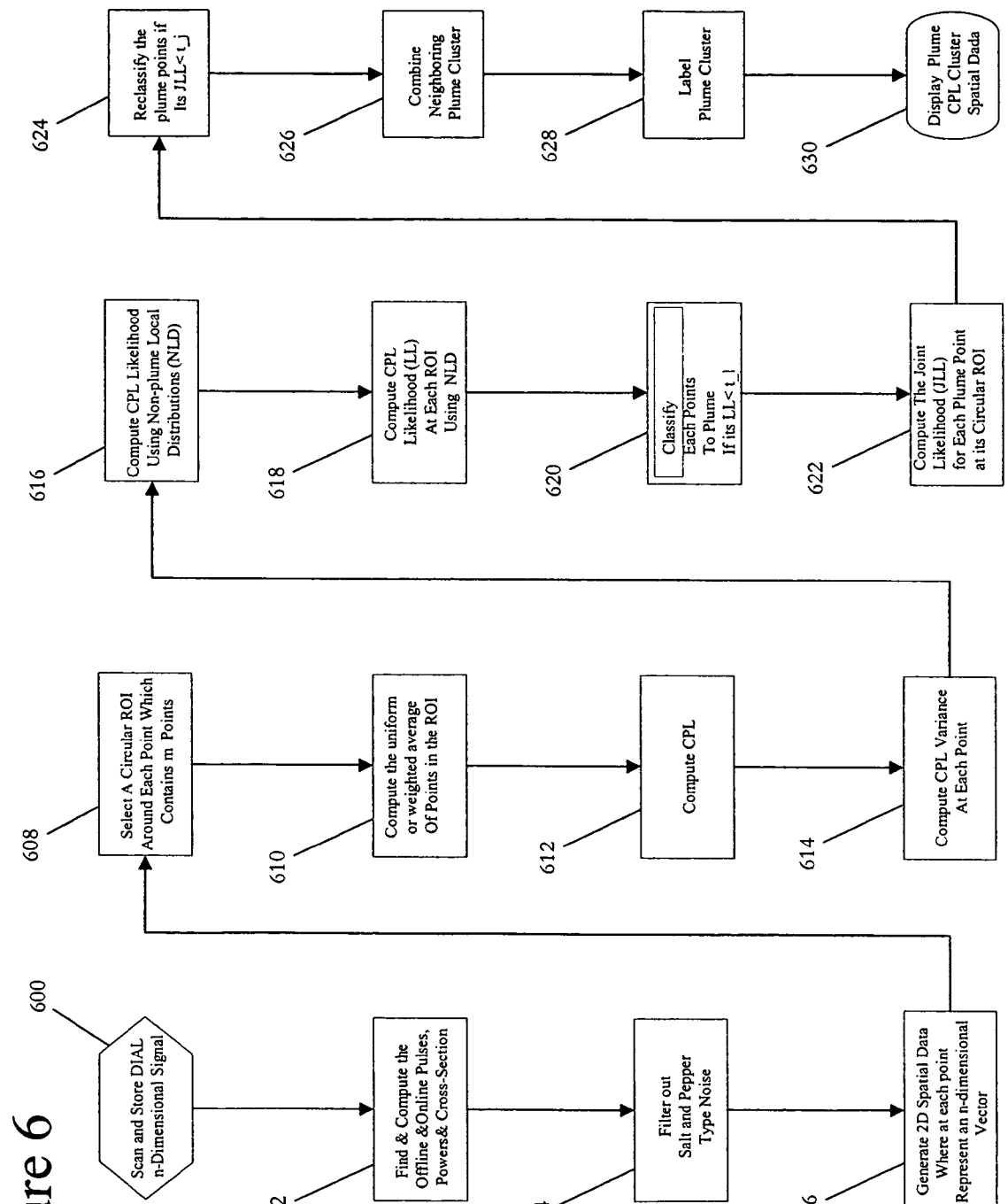
FIG. 6 is a flow chart illustrating an exemplary method of identifying plumes using a DIAL system according to the present invention.
Figure 7:
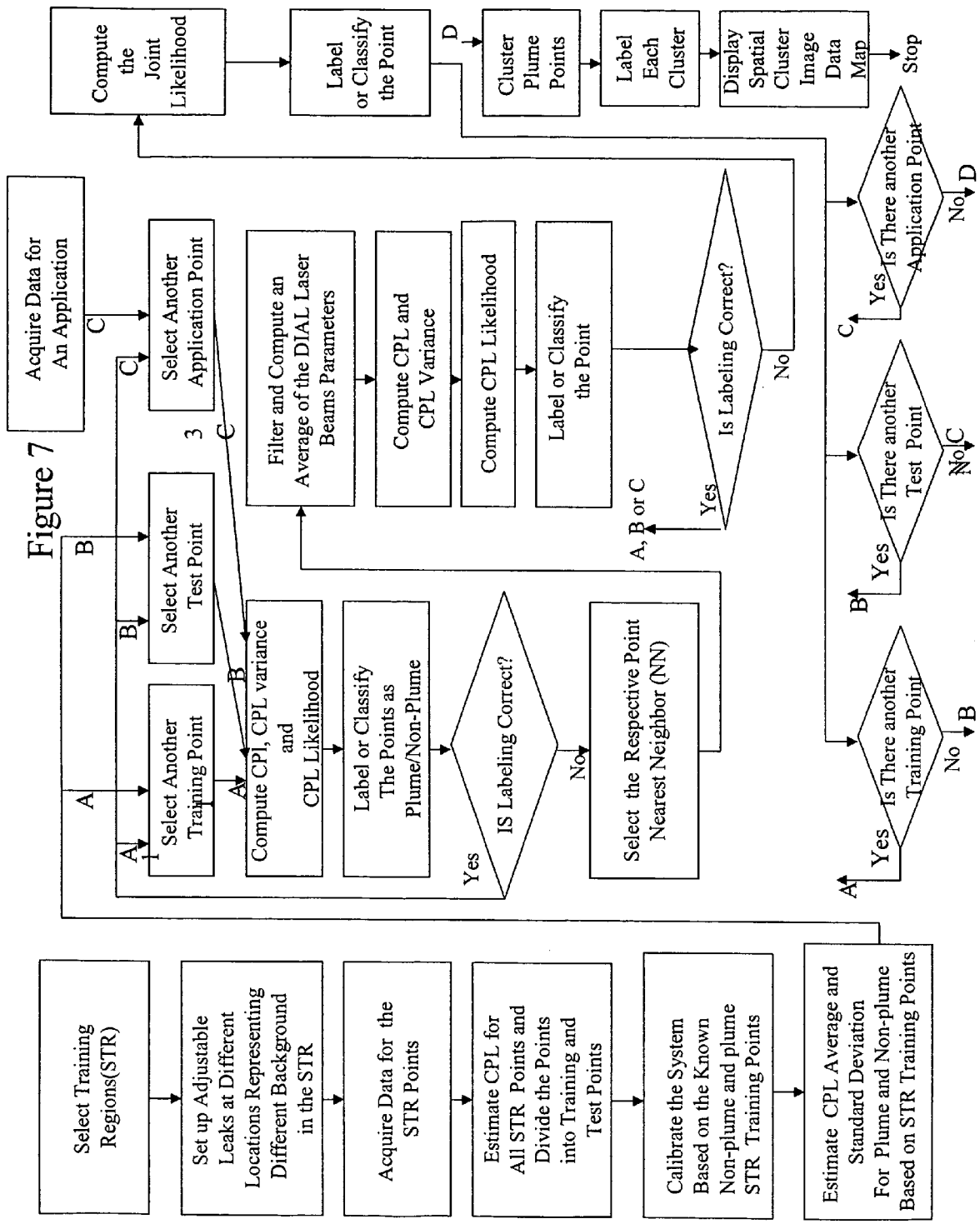
FIG. 7 is a flow chart illustrating another exemplary method of identifying plumes using a DIAL system according to the present invention.
Figure 8:
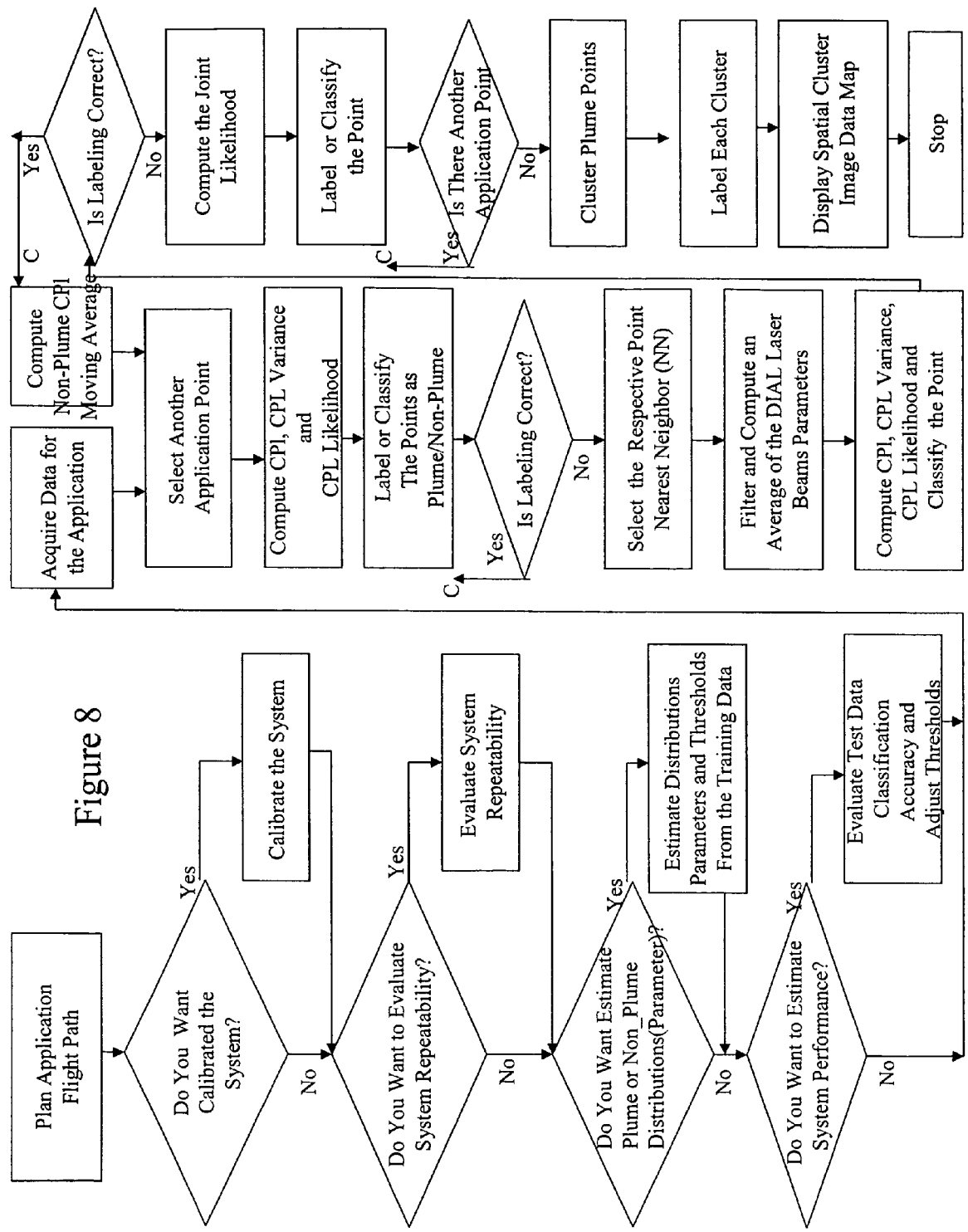
FIG. 8 is a flow chart illustrating a further exemplary method of identifying plumes using a DIAL system according to the present invention.

FIG. 6 illustrates an overview of the exemplary methods of the present invention. These exemplary methods may be performed using a DIAL system, such as the exemplary DIAL system of FIG. 1. The DIAL system is scanned through a number of measurement points and the n-dimensional signal is stored, step 600. From this n-dimensional signal, the offline and online pulses, powers, and cross-sections are found and computed, step 602. Salt and pepper type noise may be filtered out to improve the quality of the DIAL data, step 604.

Two dimensional spatial data may be generated from the DIAL signals, step 606, where each measurement point is represented by an n-dimensional vector. A circular region of interest (ROI) is selected around each measurement point, step 608. Each circular ROI desirably contains m measurement points.

An average of the data associated with the measurement points in each circular ROI is calculated, step 610. These averages may be uniform over their respective circular ROI's or the measurement points within each circular ROI may be weighted, for is example by the distance of each measurement point from the center of the ROI.

A CPL for each measurement point may then be computed, step 612, using the averaged data from step 610. As may be understood by one skilled in the art, it is desirable for the DIAL system to be calibrated before using the signals stored in step 600 to compute the CPL.

Figure 2:
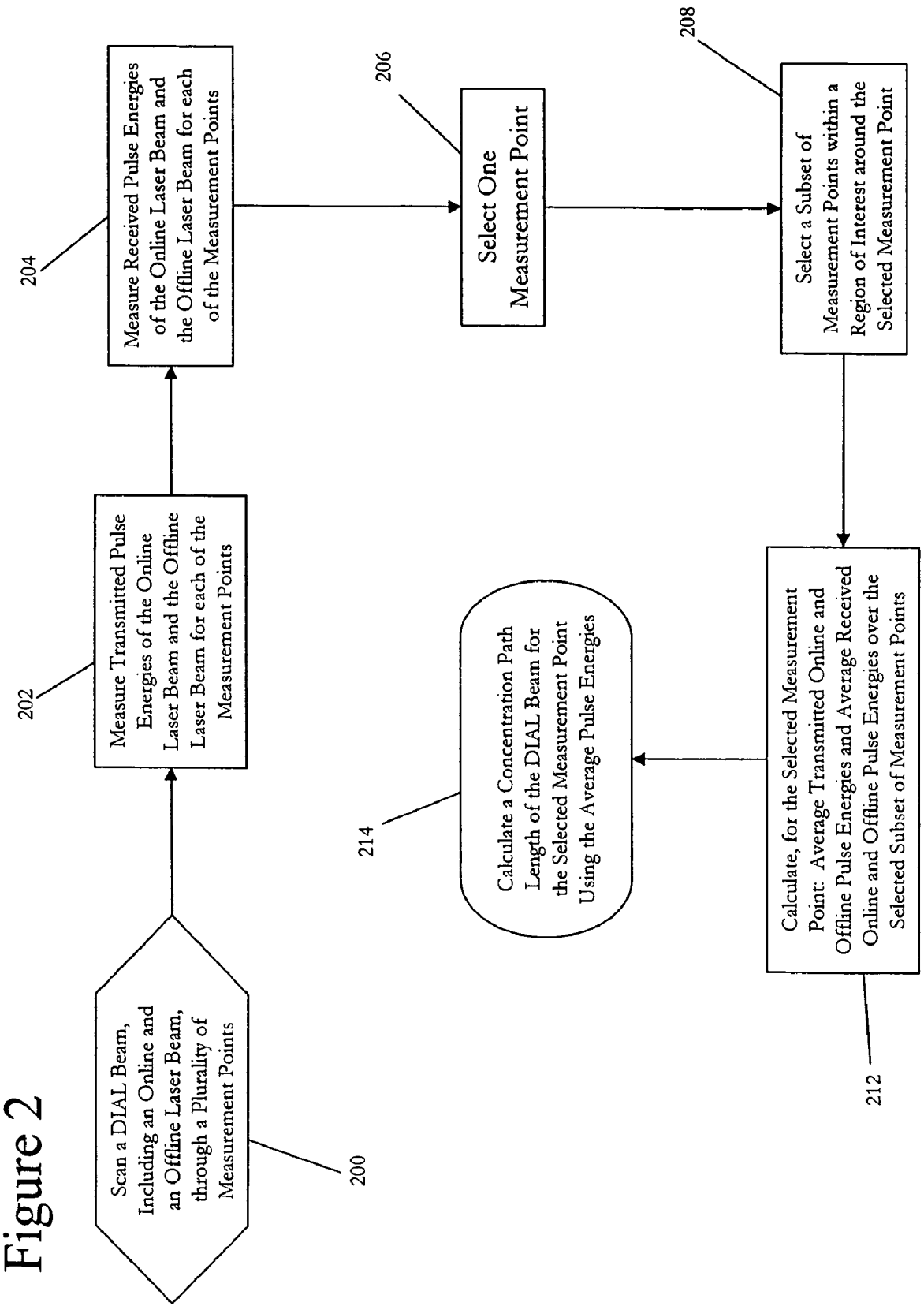
FIG. 2 is a flow chart illustrating an exemplary method of determining a concentration path length according to the present invention.

FIG. 2 illustrates, in greater detail, an exemplary method for improving the accuracy of CPL calculations for a DIAL system at a given measurement point by averaging measured pulse energy values over an ROI around the measurement point, according to the present invention.

The DIAL beam is scanned such that it is transmitted through a series of measurement points, step 200. As described above with reference to FIG. 1, the DIAL beam includes an online laser beam and an offline laser beam that are transmitted substantially collinearly. The measurement points scanned by the DIAL beam may be uniformly or non-uniformly distributed. FIG. 3A illustrates measurement points 302 arranged in exemplary uniform linear scan pattern 300 and FIG. 3B illustrates measurement points 302 arranged in exemplary non-uniform linear scan pattern 310. These scan pattern are merely illustrative and are not intended to be limiting. In particular, rectangular linear patterns as opposed to the hexagonal linear patterns shown in FIGS. 3A and 3B may be used as may scan patterns with osculating or even overlapping measurement points. It is contemplated that irregularly varying scan patterns may be used as well depending on surface conditions or other situations particular to a given DIAL application.

Figure 3C:
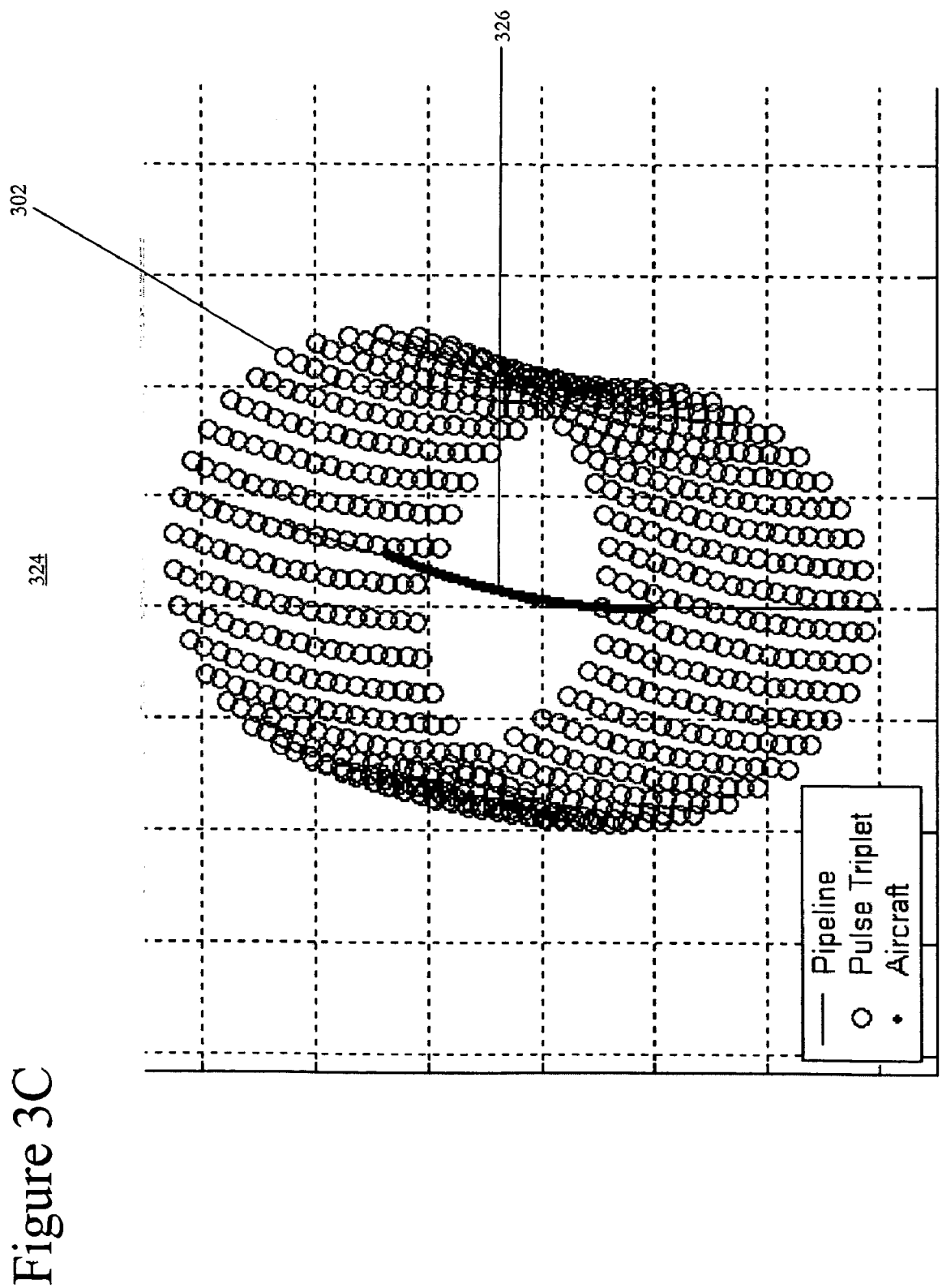
FIG. 3C is a schematic diagram illustrating variably distributed measurement points of an exemplary circular scan pattern according to the present invention.

FIG. 3C illustrates circular scan pattern 324. In this exemplary scan pattern, measurement points 302 are taken in circles as the DIAL system in moved along flight path 326. As may be seen from this example, the measurement points in circular scan pattern 324 are bunched near the edges of the scan pattern and in many cases may overlap extensively.

Transmitted pulse energies of the online laser beam and the offline laser beam corresponding to the plurality of measurement points are measured, step 202. These transmitted pulse energies are desirably stored to be used in averaging calculations. A corresponding set of received online and offline pulse energies are measured, step 204, as well. A median or other desired filter may be used on these measured pulse energies to remove salt-pepper (spike) noise in the data or to otherwise preprocess the data. Calibration corrections based on know system properties may also be performed to desirably scale the measured data.

The measurement points are then selected one at a time for averaging calculations to desirably improve the SNR of the pulse energy data, step 206. A subset of measurement points within an ROI around the selected measurement point are selected, step 208. FIGS. 3A and 3B illustrate exemplary ROI's for three exemplary measurement points. In FIG. 3A, with uniformly distributed measurement points 302, ROI 304 is shown around selected measurement point 306, shown in black. The subset of measurement points in ROI 304 includes selected point 306 and 36 nearest neighbor points 306, shown in grey for clarity. FIG. 3B illustrates two ROI's 312 and 318 around selected measurement points 314 and 320, respectively, each including 36 nearest neighbor points 316 and 322. As shown in FIG. 3B, ROI 318 is larger than ROI 312 and nearest neighbor points 322 are slightly differently arranged because of the varying distribution of measurement points 302 in the X direction of scan pattern 310. In this example, the ROI size is varied such that the number of nearest neighbor points remains constant. It is contemplated that, alternatively, the ROI could remain constant and the number of the number of nearest neighbor points included in the subset could vary instead when a non-uniform scan pattern is used.

It is noted that, although ROI's that include 36 nearest neighbor points are shown in the exemplary embodiments of FIGS. 3A and 3B, ROI's that include other numbers of nearest neighbor points may be used. For example, in an exemplary linear scan pattern with osculating measurement points, an ROI with a radius approximately five times a beam radius of the DIAL beam may desirably enclose about 25 measurement points, the selected point and about 24 nearest neighbor points. The desired radius of the ROI in various scan patterns may be learned from the parameters of the DIAL system and stored in a look-up table based on the density of the point of a fixed initial ROI circle or may be adaptively determined from the DIAL data.

Using the ROI subset of measurement points average values of the various pulse energies are calculated, step 212. The average transmitted online pulse energy is calculated from the transmitted pulse energies of the online laser beam of the selected ROI subset of the measurement points. The average transmitted offline pulse energy is calculated from the transmitted pulse energies of the offline laser beam of the selected ROI subset of the measurement points. The average received online pulse energy is calculated from the received pulse energies of the online laser beam of the selected ROI subset of the measurement points. And the average received offline pulse energy is calculated from the received pulse energies of the offline laser beam of the selected ROI subset of the measurement points. Uniform, unweighted, or weighted averaging may be used in these pulse energies to improve SNR of the DIAL data. This operation may also be understood as a convolution between a low pass filter and a signal, an image, or general spatial data.

The uniform averaging means all n Nearest Neighboring (NN) points surrounding the point of interest are equally weighted to compute the average:

$$\frac{1}{(n+1)}\sum_{K=0}^{n} E_{i_K}, \quad \text{Eq. (2)}$$

where $E_{i_K}$ is a measured pulse energy value for the $K^{th}$ point of the ROI subset around selected point i and $E_{i_0}$ is the measured pulse energy value of the selected measurement point.

The weighted averaging means the weight of the filter or the NN are not uniform, for example, the weighting could based on the distance between the selected point and a NN point. A Gaussian kernel is one such exemplary weighting function. If a circular scanner is used in the DIAL system to collect the pulse energy data, use of the Gaussian kernel may be desirable. In this situation the density of measurement point sampling may not be uniform across the scanned area or the ROI and the Gaussian kernel allows closer NN points to have more effect on the average.

Once the measurement points in the ROI subset for a given measurement point are determined, the corresponding pulse energies may be convolved with a circular Gaussian Kernel to calculate the weighted average:

$$\exp\left(-\left[\frac{(X_{i_K} - X_{i_0})^2 + (Y_{i_K} - Y_{i_0})^2}{2\sigma^2}\right]\right), \quad \text{Eq. (3)}$$

start with $\sigma = 1$, or in case of different scaling in the X and Y dimensions:

$$\exp\left(-\left[\frac{(X_{i_K} - X_{i_0})^2}{2\sigma_x^2}\right]\right)\exp\left(-\left[\frac{(Y_{i_K} - Y_{i_0})^2}{2\sigma_y^2}\right]\right), \quad \text{Eq. (3a)}$$

where the index $i_0$ represents the selected measurement point and $i_K$ represents one of the n-NN points in the ROI subset. Therefore the $i_0$ point weight is 1. It is noted that the convolution is desirably normalized to accomplish the spatial averaging.

For example, let $E_{i_K}^{on-r}$ be the online received energy of the $K^{th}$ point in the ROI subset. The Gaussian weighted spatial averaging over the n-NN points may then be computed by:

$$\frac{1}{\sum_{K=0}^{n}\exp\left(-\left[\frac{(X_{i_K} - X_{i_0})^2 + (Y_{i_K} - Y_{i_0})^2}{2\sigma^2}\right]\right)} \quad \text{Eq. (4)}$$

$$\left\{\sum_{K=0}^{n} E_{i_k}^{on-r} * \exp\left(-\left[\frac{(X_{i_K} - X_{i_0})^2 + (Y_{i_K} - Y_{i_0})^2}{2\sigma^2}\right]\right)\right\},$$

These average pulse energy values of the selected point (the average transmitted online pulse energy, the average transmitted offline pulse energy, the average received online pulse energy, and the average received offline pulse energy) are used to calculate a concentration path length (CPL) of the DIAL beam for the one selected measurement point, step 214. This calculation may be performed using the DIAL equation, Equation 1.

The next measurement point may be selected and steps 208, 212 and 214 may be repeated until CPL's for all of the measurement points have been calculated. It is noted that steps 208, 212, and 214 may be performed for different measurement points in is parallel, but these steps are described in the exemplary method of FIG. 2 as being performed for different measurement points in series for illustrative purposes.

Returning to FIG. 6, once the CPL of a measurement point is calculated the next step is to determine whether the measurement point represents a plume point or a non-plume point. To help overcome low SNR's of the DIAL signals, a probabilistic approach may be used to determine whether the measurement point represents a plume point or a non-plume point.

A CPL variance may be calculated at each measurement point, step 614, based on first order error propagation. A CPL likelihood threshold may be calculated for each measurement point, step 616, using a non-plume local distribution. Methods of determining this non-plume local distribution are described below with reference to FIG. 4. A CPL likelihood may be calculated for each measurement point as well, step 618, using the ROI.

The measurement points may then be classified as plume or non-plume points, step 620, based on a comparison of the CPL likelihood of each measurement point to the corresponding CPL likelihood threshold.

FIG. 4 illustrates, in detail, two such exemplary methods to determine whether the measurement point represents a plume point or a non-plume point based on the CPL of the measurement point, according to the present invention.

Let $P(\omega_1), P(\omega_2), p(X|\omega_1), p(X|\omega_2)$ be the prior probability and probability density function of class 1 (background: non-plume) and class 2 (target: plume) respectability.

The Bayes Rule for making a determination may be stated as: If $p(X|\omega_1)P(\omega_1) > p(X|\omega_2)P(\omega_2)$, then X is classified to class 1, otherwise X is classified to class 2.

This Bayes Rule may be rewritten as follows: If $$\ln[p(X|\omega_1)P(\omega_1)] > \ln[p(X|\omega_2)P(\omega_2)] \Rightarrow$$

$$\ln\left[\frac{P(\omega_1)}{P(\omega_2)}\right] + \ln\left[\frac{p(X|\omega_1)}{p(X|\omega_2)}\right] > 0,$$

then X is classified to class 1 otherwise to class 2.

This rule is called Maximum Likelihood Rule (MLR). If it is assumed that the probability density functions for class 1 and 2 are normally distributed, then the MLR may be written as:

$$\ln\left[\frac{P(\omega_1)}{P(\omega_2)}\right] + \ln\left[\frac{\sigma_2}{\sigma_1}\right] - \frac{1}{2}\left(\frac{X-\overline{X_1}}{\sigma_1}\right)^2 + \frac{1}{2}\left(\frac{X-\overline{X_2}}{\sigma_2}\right)^2 > 0 \Rightarrow X \to \omega_1, \quad \text{Eq. (5)}$$

where the parameters $(\overline{X_1}, \sigma_1)$ and $(\overline{X_2}, \sigma_2)$ are the mean and standard deviation of classes 1 and 2, respectively.

Among the exemplary embodiments of the present invention are methods to detect a gas leak using an image generated from a DIAL signal data set. Two such exemplary methods are shown in FIG. 4. In these methods, the CPL's of a plurality of measurement points are determined, step 400. This determination may be made using the exemplary method of FIG. 2 or may be made using the measured pulse energy data.

If it is assumed that the CPL's collected include both non-plume and plume distributions and furthermore, it is assumed that the CPL values are normally distributed and that the mean and standard deviation of these two distributions are known, then the MLR may be written as:

$$\ln\left[\frac{P(\text{nonplume})}{P(\text{plume})}\right] + \ln\left[\frac{CPL_{sd\_plume}}{CPL_{sd\_nonplume}}\right] - \frac{1}{2}\left(\frac{cpl - \overline{CPL_{nonplume}}}{CPL_{sd\_nonplume}}\right)^2 + \frac{1}{2}\left(\frac{cpl - \overline{CPL_{plume}}}{CPL_{sd\_plume}}\right)^2 > 0 \Rightarrow . \quad \text{Eq. (6)}$$

$$cpl \to \text{nonplume}$$

It may very expensive and difficult to collect and characterize plume (target) CPL sample points to estimate ($\overline{CPL_{plume}}, CPL_{sd\_plume}$). However, it may be relatively easy to collect non-plume (background CPL) sample points to mainly estimate the local average background CPL ($CPL_{nonplume}$). For example, a set of non-plume sample points may be measured in a nearby area, which is known not to have any plumes. Alternatively, obvious a set non-plume points within the measurement points may be identified. These non-plume local distributions may then be averaged.

The average CPL for non-plume is about the concentration of the background target gas times the range (altitude). In practice, though, the surface cover type reflectivity, low SNR and other source interference noises may make the background (clutter) CPL variably larger.

Assuming a normal distribution of the non-plume suggests that using the following probabilities or equivalent likelihoods may be desirable:

$$CPL\_PR\_1 = \text{Probability}[(\overline{cpl} - cpl_{sigma}) < cpl < (\overline{cpl} + cpl_{sigma})] = 0.683; \quad \text{Eq. (7)}$$

$$CPL\_LL\_1 = \ln(CPL\_PR\_1) = -0.3813; \quad \text{Eq. (8)}$$

$$CPL\_PR = \text{Probability}[(\overline{cpl} - 2*cpl_{sigma}) < cpl < (\overline{cpl} + 2*cpl_{sigma})] = 0.954; \quad \text{Eq. (9)}$$

$$CPL\_LL\_2 = \ln(CPL\_PR\_2) = -0.0471; \quad \text{Eq. (10)}$$

$$CPL\_PR = \text{Probability}[(\overline{cpl} - 3*cpl_{sigma}) < cpl < (\overline{cpl} + 3*cpl_{sigma})] = 0.997; \text{ and} \quad \text{Eq. (11)}$$

$$CPL\_LL\_3 = \ln(CPL\_PR\_3) = -0.0030; \quad \text{Eq. (12)}$$

So, for example, if the probability of the estimated Concentration Path Length is less than 0.997 or the CPL Likelihood value is less than −0.0030, then it may be desirable to determine that the estimated CPL is from a non-plume.

It is noted that $cpl_{sigma} = cpl_{sd}$, however, in the situations where:

$$\text{Prob.}[cpl > (\overline{cpl} + n*cpl_{sigma})] < \frac{\{1 - \text{Prob.}[cpl < (\overline{cpl} - n*cpl_{sigma}) cpl < (\overline{cpl} + n*cpl_{sigma})]\}}{2}; \quad \text{Eq. (13)}$$

$$\text{Probability}[cpl > (\overline{cpl} + n*cpl_{sigma})] < \frac{1}{2} - \{\text{Probability}[\overline{cpl} < cpl < (\overline{cpl} + n*cpl_{sigma})]\}; \text{ or} \quad \text{Eq. (14)}$$

$$CPL\_LL\_n > \ln\{\text{Probability}[\overline{cpl} < cpl > (\overline{cpl} + n*cpl_{sigma})]\}, \quad \text{Eq. (15)}$$

the estimated cpl may be determined to represent a plume distribution.

Furthermore, since the error in estimating CPL is larger when SNR is low, i.e. when the returned signals are low, and the error is low when the SNR is high, i.e. the returned signals are high, the mean of CPL may be estimated based on local non-plume CPL samples and the standard deviation of the CPL may be adaptively estimated for each sample. Therefore, a decision rule may be created based on Equations 13-15 and using local average CPL and standard deviation values.

A local subset of measurement points around each measurement point is identified to be used to generate a local CPL average for each measurement point. This local subset is selected similarly to the ROI subset described above with reference to FIGS. 3A and 3B. If the exemplary method of FIG. 2 is used to determine the CPL's of the measurement points, the local subset may be the same as the ROI subset used in these calculations, but this is not necessary.

An average CPL of each local subset is calculated, step 402. The CPL standard deviation of each local subset may be calculated, step 404, based on first order error propagation. An exemplary method of calculating these CPL standard deviations is described below with reference to Eqs. 29-33a.

These local subset values may be used in the following decision rule to compute a likelihood value, step 408, to label each measurement point in the DIAL data set as a plume point or a non-plume only based on local non-plume distribution. These likelihood values, CPL_LL, may be determined using:

$$\text{CPL\_LL} = -\frac{1}{2}\ln(2\Pi) - \ln[p(cpl \mid \text{nonplume})] = \quad \text{Eq. (16)}$$

$$\ln(CPL_{sd}) - \frac{1}{2}\left(\frac{cpl - \overline{CPL}}{CPL_{sd}}\right)^2.$$

The likelihood values of the various measurement points may then be compared to a CPL threshold level:

$$\text{CPL\_LL}_{threshold} = \ln[p(\overline{CPL} + T*CPL_{sd} \mid \text{nonplume})] = \quad \text{Eq. (17)}$$

$$-\frac{1}{2}\ln(2\Pi) - \ln(CPL_{sd}) - \frac{1}{2}(T)^2,$$

where T is a threshold standard deviation level.

If the CPL likelihood value for a measurement point is less than the CPL threshold level for that point, then measurement point is determined to be a non-plume point, step 410. This rule, known as the Hooshmand decision rule (HDR) may be written as:

$$\text{CPL\_LL} < \text{CPL\_LL}_{threshold} \Rightarrow cpl \rightarrow \text{plume}. \quad \text{Eq. (18)}$$

Subtracting the identical constant terms from CPL_LL and CPL_LL$_{threshold}$ leads to the following:

$$\text{CPL\_LL} = -\ln(CPL_{sd}) - \frac{1}{2}\left(\frac{cpl - \overline{CPL}}{CPL_{sd}}\right)^2 \text{ and} \quad \text{Eq. (19)}$$

$$\text{CPL\_LL}_{threshold} = -\ln(CPL_{sd}) - \frac{1}{2}T^2. \quad \text{Eq. (20)}$$

Removing the common first terms in Equations 19 and 20 and substituting the remaining terms into Equation (18) leads to:

$$-\frac{1}{2}\left(\frac{cpl - \overline{CPL}}{CPL_{sd}}\right)^2 < -\frac{1}{2}(T)^2, \quad \text{Eq. (21)}$$

and then multiplying both sides by −2 provides a calculationally simplified version of the HDR:

$$\text{If } \left(\frac{cpl - \overline{CPL}}{CPL_{sd}}\right)^2 > (T)^2 \Rightarrow \text{plume} \quad \text{Eq. (22)}$$

$$\text{Else} \Rightarrow \text{Non-Plume}$$

or equivalently:

$$\text{If } \left(\frac{cpl - \overline{CPL}}{CPL_{sd}}\right)^2 > T \Rightarrow \text{Plume} \quad \text{Eq. (22a)}$$

$$\text{Else} \Rightarrow \text{Non-Plume}$$

where $\overline{CPL}$ is estimated from the previously collected non-plume training samples or adaptively estimated based on moving average of highly likely non-plume classified points and ($CPL_{sd}$) is estimated based on Eqs. 33 and 33a.

This calculationally simplified version of the HDR may be used to determine whether a measurement point represents a plume point or a non-plume point, step 406, without first calculating the full CPL likelihood value and CPL threshold level of each measurement point.

Returning to FIG. 6, another issue that may arise when measurement points are classified to be plume or non-plume point based on DIAL data with a low SNR is that the classification may be wrong. For measurement points falsely classified as non-plume points, the false classification may not pose a significant problem, particularly if several nearby measurement points are correctly classified as plume points, which may often happen. For measurement points falsely classified as plume points, however, the false classification may pose a significant problem. This is because such false alarms may lead to the shut down of a pipeline or other precautionary or remedial measures.

The potential for false alarms always exists when the measurement points are classified based on a probabilistic criterion, such as the HDR described above. Therefore, it may be desirable to use spatial information to reduce the potential labeling inaccuracies, i.e. the number of false alarms.

To accomplish this goal, the joint likelihood for each previously identified plume point at its circular ROI may be computed, step 622. The previously identified plume points may then be reclassified, step 624, based on a comparison of their joint likelihood to the CPL likelihood threshold.

FIG. 5 illustrates, in detail, an exemplary method for reducing the number of false alarms, according to the present invention. In this exemplary method, the CPL's of a plurality of measurement points are determined, step 500. As in the exemplary methods of FIG. 4, this determination may be made using the exemplary method of FIG. 2 or may be made using the measured pulse energy data. A preliminary determination of whether each measurement point represents a plume or a non-plume point is made, step 502. It is noted that measurement points may be determined to be too close to label at this stage of the exemplary method. Such points may be identified as uncertain labeled points. The classification of each measurement point may desirably be made using one of the exemplary methods of FIG. 4, but other methods to determine whether the measurement points represents plume or a non-plume points may be used as well.

One of the measurement points identified as a plume point or an uncertain labeled point, the $i^{th}$ measurement point, is selected, step 504, and a nearest neighbor subset of measurement points around the $i^{th}$ measurement point is identified. The nearest neighbor subset of measurement points includes K measurement points, which, if the exemplary methods of either FIG. 2 or FIG. 4 are used, may be the same K measurement points as one or both of the subsets used in the exemplary methods of FIG. 2 and/or FIG. 4 but this is not necessary. It is noted that the exemplary method of FIG. 5 may be used to classify uncertain labeled points, in which case only uncertain labeled points are selected in step 504, or to test for false plume points, in which case only plume points are selected in step 504, or the exemplary method of FIG. 5 may be used to both classify uncertain labeled points and test for false plume points, in which case both uncertain labeled points and plume points are selected in step 504.

Let $\{cpl_{ij}=1, 2, \ldots K\}$ be the CPL's of the spatial K-NN nearest neighbor subset of measurement points around the $i^{th}$ measurement point. Therefore:

$$(CPL\_LL)_i = p(cpl_{i1}, cpl_{i2}, \ldots cpl_{iK}|nonplume). \quad \text{Eq. (23)}$$

If it is assumed that the joint probability function of the nearest neighbor subset of measurement point is independently and normally distributed, then Equation 23 may be rewritten as:

$$(CPL\_LL)_i = \prod_{j=1}^{K} p(cpl_{ij} | nonplume); \quad \text{Eq. (24)}$$

$$(CPL\_LL)_i = \ln\left[\prod_{j=1}^{K} p(cpl_{ij} | nonplume)\right] = \sum_{j=1}^{K} p(cpl_{ij} | nonplume); \text{ or} \quad \text{Eq. (25)}$$

$$(CPL\_LL)_i = -\sum_{j=1}^{K} \ln(CPL_{sd})_j - \frac{1}{2}\sum_{j=1}^{K} \left[\frac{cpl_{ij} - \overline{CPL}}{(CPL_{sd})_j}\right]^2. \quad \text{Eq. (26)}$$

Similarly, a corresponding CPL threshold level may be calculated, by:

$$(CPL\_LL)_{Threshold} = -\sum_{j=1}^{K} \ln(CPL_{sd})_j - \frac{1}{2}\sum_{j=1}^{K} T^2 = -\sum_{j=1}^{K} \ln(CPL_{sd})_j - \frac{1}{2}KT^2. \quad \text{Eq. (27)}$$

Once again by removing the common first terms in Equations 26 and 27 leads HDR:

$$\frac{1}{K}\sum_{j=1}^{K} \left[\frac{cpl_{ij} - \overline{CPL}}{(CPL_{sd})_j}\right]^2 > T^2 \Rightarrow \text{Plume} \quad \text{Eq. (28)}$$

If Else ⇒ Non-Plume, or:

$$\sqrt{\frac{1}{K}\sum_{j=1}^{K} \left[\frac{cpl_{ij} - \overline{CPL}}{(CPL_{sd})_j}\right]^2} > T \Rightarrow \text{Plume} \quad \text{Eq. (28a)}$$

If Else ⇒ Non-Plume, where $\overline{CPL}$ is estimated from the previously collected non-plume training samples or adaptively estimated based on the moving average of highly likely non-plume classified points and $(CPL_{sd})$ is estimated based on Eqs. 33 and 33a.

To utilize Equations 26 and 27, one nearest neighbor point, the $j^{th}$ measurement point, of the nearest neighbor subset is selected, step 506. A moving average CPL, $\overline{CPL_{ij}}$, of the CPL's of a local subset of classified highly likely non-plume measurement points around the $j^{th}$ measurement point is adaptively calculated, step 508, and a standard deviation, $(CPL_{sd})_j$, of the CPL's of each measurement point in the nearest neighbor subset is calculated based on Eqs. 33 and 33a, step 510. This local subset of measurement points may be the same size as the nearest neighbor subset, but this is not necessary. For example, some of the points in the nearest neighborhood set may be filtered out.

It is then determined whether the $\overline{CPL_{ij}}$ and the $(CPL_{sd})_j$ for all of the measurement points in the local subset have been calculated, step 512. If they have not, steps 506, 508, 510, and 512 are repeated. If they have, the CPL joint likelihood value for the selected plume point may be calculated using Equation 26, step 514.

The CPL joint likelihood value of the selected plume point is compared to the corresponding CPL threshold level, as above in the HDR, to determine whether the selected point is a plume or non-plume point, step 516. If the selected point is determined to be a non-plume point, then it is labeled as a non-plume point, and it is determined to be a plume point, then it is labeled as a plume point.

It is then determined if all of the plume and/or uncertain labeled points have been tested, step 518. If all of the desired points have not been tested, then another point is selected, step 504 and the process repeated. If all of the desired points have been tested, then all remaining plume points are considered true plume points and the exemplary method is complete, step 520.

Returning to FIG. 6, once the reclassified plume points have been determined, these points may be combined with neighboring plume points to form neighboring plume clusters, step 626. Each of these neighboring plume clusters may be labeled, step 628, so that the various neighboring plume clusters may be identified by the label. It is noted that plume points that do not have any neighboring plume points may be suspect and additional scrutiny of such lone plume points to verify that they are not false plume points may be desirable.

The plume CPL clusters may then be displayed using the associated spatial data, step 630, to visually indicate the location and extent of each plume.

Based on a first-order error propagation, a CPL variance may be calculated by:

$$CPL_{var} = \left[\frac{1}{2\Delta C_\sigma}\right]^2 \left\{\left[\frac{\sigma_{noise}^2}{(E_{off}^r)^2}\right] + \left[\frac{\sigma_{noise}^2}{(E_{on}^r)^2}\right] + \left[\frac{\sigma_{noise}^2}{(E_{off}^t)^2}\right] + \left[\frac{\sigma_{noise}^2}{(E_{on}^t)^2}\right] + \text{COVARIANCE\_TERMS}\right\},$$

Eq. (29)

or equivalently:

$$CPL_{var} = \left[\frac{1}{2\Delta C_\sigma}\right]^2 \left\{\left[\frac{1}{SNR_{off}^r}\right]^2 + \left[\frac{1}{SNR_{on}^r}\right]^2 + \left[\frac{1}{SNR_{off}^t}\right]^2 + \left[\frac{1}{SNR_{on}^t}\right]^2 + \text{COVARIANCE\_TERMS}\right\}$$

Eq. (29a)

Because $\left[\frac{1}{SNR_{off}^t}\right]^2$, $\left[\frac{1}{SNR_{off}^t}\right]^2$ and COVARIANCE_TERMS are relatively very small, then CPL variance at each point is estimated by:

$$CPL_{var} = \left[\frac{1}{2\Delta C_\sigma}\right]^2 \left\{\left[\frac{1}{SNR_{off}^r}\right]^2 + \left[\frac{1}{SNR_{on}^r}\right]^2\right\},$$

Eq. (30)

and the CPL standard deviation, $CPL_{sd}$, is estimated by:

$$(CPL_{sd}) = \sqrt{CPL_{var}} = \left[\frac{1}{2\Delta C_\sigma}\right] \sqrt{\left\{\left[\frac{1}{SNR_{off}^r}\right]^2 + \left[\frac{1}{SNR_{on}^r}\right]^2\right\}}.$$

Eq. (31)

In practice $CPL_{sd}$ may be estimated from the transmitted online and offline laser pulse energy or average power, the returned offline energy or average power, the filtered and average cross section, and average CPL based on the following derivations (It is noted that, for the sake of brevity in the following equations, the subscripts f and o are used to indicate the offline and online related measurements, respectively, and the superscripts t and r are used to indicate the transmitted and received related measurements, respectively.):

$$cpl = \frac{1}{2[\Delta C_\sigma]}\left[\ln\frac{\frac{E_f^r}{E_f^t}}{\frac{E_o^r}{E_o^t}}\right] = \frac{1}{2[\Delta C_\sigma]}\left[\ln\frac{E_f^r}{E_o^r}\frac{E_o^t}{E_f^t}\right]$$

Eq. (32)

Note:

$\Delta C_\sigma = \sigma(\lambda_o) - \sigma(\lambda_f)$

Assuming $\sigma(\lambda_f) \sim 0 \Rightarrow \Delta C_\sigma = \sigma(\lambda_o) \Rightarrow$ -continued $$\frac{E_f^r}{E_o^r} = \frac{E_f^t}{E_o^t}\exp[2\sigma(\lambda_o)cpl]$$

$$\left[\frac{E_f^r}{E_o^r}\right]^2 = \left[\frac{E_f^t}{E_o^t}\right]^2 \exp[4\sigma(\lambda_o)cpl]$$

Therefore, Eq. 31 may be rewritten as:

$$CPL_{sd} = \frac{Noise_{sd}}{2\sigma(\lambda_o)}\sqrt{\left[\frac{1}{(E_f^r)^2} + \frac{1}{(E_o^r)^2}\right]} =$$

$$\frac{Noise_{sd}}{2\sigma(\lambda_o)E_f^r}\sqrt{\left[1 + \left[\frac{E_f^t}{E_o^t}\right]^2 \exp[4\sigma(\lambda_o)cpl]\right]}, \text{ or:}$$

Eq. (33)

$$CPL_{sd} = \frac{1}{2\sigma(\lambda_o)SNR_f^r}\sqrt{\left[1 + \left[\frac{E_f^t}{E_o^t}\right]^2 \exp[4\sigma(\lambda_o)cpl]\right]}.$$

Eq. (33a)

This may lead to the following observations:
1. When SNR is high, distributions of $$\frac{E_f^r}{E_f^t}, \frac{E_o^r}{E_o^t}, \text{ or } \frac{E_f^r}{E_f^t} * \frac{E_f^t}{E_o^t}$$

or their log distributions may desirably be used to detect the non-plume or plume point. Unfortunately, in practice, variable background clutter may significantly reduce the SNR and, therefore, make the accurate classification of measurement point a difficult problem to solve.
2. In Eqs. 33 and 33a, the average of a filtered $\sigma(\lambda_o)$ in a nearest neighborhood subset may desirably be used as a local improved estimate of the cross-section.
3. In Eqs. 33 and 33a, the average of highly likely non-plume CPL's in a nearest neighborhood subset may be used as a local improved estimate of the non-plume CPL average.
4. Eqs. 33 and 33a suggest that the lower the surface reflectivity becomes, the lower $E_f^r$ becomes and the higher $CPL_{sd}$ becomes. The opposite is true as well. (I.E. the higher the surface reflectivity becomes, the higher $E_f^r$ becomes and the lower $CPL_{sd}$ becomes.)
5. It is noted that the unit of the CPL is the inverse of cross-section unit. In Eqs. 33 and 33a the cross-section unit is m$^2$/molecule. Therefore the CPL unit is molecule/m$^2$. However, in the above equations, this unit may be converted to ppm-m by replacing $\sigma(\lambda_o)$ with $$\sigma(\lambda_o)\frac{N_a}{10^6},$$

where $N_a$ is the air density.
6. Ideally, the non-plume CPL should be ~0, but because of variations of surface cover type reflectivity, as has been previously noted, $E_f^r$ varies accordingly and this variation leads to non-zero non-plume CPL values.
7. An exemplary DIAL system may be calibrated for each target gas based on available known plume point values having selected known background surface reflectivity values. These values may be used to estimate additive and multiplicative calibration coefficients. However, it is noted that the additive calibration factor may not allow correction for surface cover type related variable modulated CPL bias.

8. Furthermore, it is noted that, instead of the single point based derived likelihood rules of Eqs. 22 and 22a and the derived joint likelihood rule of Eqs. 28 and 28a, a T-test or ANNOVA test may also be used to label whether an estimated CPL is coming from a non-plume family distribution or a plume family distribution.

9. The local CPL sample mean may also be used in a T-test or ANNOVA test to label whether an estimated local CPL sample mean, in a nearest neighborhood subset, is coming from a non-plume family distribution or plume family distribution.

As noted above, in Eqs. 33 and 33a, the $CPL_{sd}$ unit is m$^2$/molecule. Eqs. 34 and 35 may be used to calculate CPL and $CPL_{sd}$ in units of ppm-m.

$$cpl = \frac{1}{2[10^{-6}N_a\sigma(\lambda_o)]}\left[\ln\frac{E_f^r}{E_o^r}\frac{E_o^t}{E_f^t}\right], \quad \text{Eq. (34)}$$

$$CPL_{sd} = \frac{1}{2[10^{-6}N_a\sigma(\lambda_o)]SNR_f^r} \sqrt{\left[1 + \left[\frac{E_f^t}{E_o^t}\right]^2 \exp\{4[10^{-6}N_a\sigma(\lambda_o)cpl]\}\right]}, \quad \text{Eq. (35)}$$

A first order approximation of Eq. 35 is derived below to provide a better understanding of the decision rule. This approximation begins by assuming $$\left[\frac{E_f^t}{E_o^t}\right] \sim 1.$$

In this limit:

$$\sqrt{\left[1 + \left[\frac{E_f^t}{E_o^t}\right]^2 \exp\{4[10^{-6}N_a\sigma(\lambda_o)CPL]\}\right]} \approx \quad \text{Eq. 36}$$

$$\exp\{2[10^{-6}N_a\sigma(\lambda_o)CPL]\}1 + 2[10^{-6}N_a\sigma(\lambda_o)cpl] + \exp\{2[10^{-6}N_a\sigma(\lambda_o)cpl]\}, \text{ and}$$

... (Taylor series approximation).

Continuing this approximation for the case when $2[10^{-6}N_a\sigma(\lambda_o)cpl]\gg1$, yields:

$$1+2[10^{-6}N_a\sigma(\lambda_o)cpl]\approx 2[10^{-6}N_a\sigma(\lambda_o)cpl]. \quad \text{Eq. 37}$$

Based on the approximation of Eq. 37, Eq. 35 may be reduced to Eq. 38:

$$CPL_{sd} = \frac{cpl}{SNR_f^r}. \quad \text{Eq. 38}$$

Based on this approximation, $CPL_{sd}$ for the single point based and Nearest Neighbor (NN) or the joint decision rule may be give by:

$$\text{If } SNR_f^r\left(\frac{cpl - \overline{CPL}}{cpl}\right) > T \Rightarrow \text{Plume}, \quad \text{Eq. (39)}$$

Else ⇒ Non-Plume

Or:

$$\text{If } \left(\frac{cpl - \overline{CPL}}{cpl}\right) > \frac{T}{SNR_f^r} \Rightarrow \text{Plume}. \quad \text{Eq. (39a)}$$

Else ⇒ Non-Plume

Similarly, the NN based decision rule may be given by:

$$\text{If } \sqrt{\frac{1}{K}\sum_{j=1}^{K}\left\{[SNR_f^r]_{ij}\left[\frac{cpl_{ij} - \overline{CPL}}{cpl_{ij}}\right]\right\}^2} > T \Rightarrow \text{Plume}, \quad \text{Eq. (40)}$$

Else ⇒ Non-Plume

The present invention includes exemplary methods to improve the SNR of data in exemplary DIAL systems. These exemplary methods allow increased accuracy in the identification of plume points by exemplary DIAL systems. Such techniques may be useful in a number of technologies, such as remote sensing of chemical leaks and contamination. Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for improving the calculation of a concentration path length (CPL) of a DIAL beam in a differential absorption LIDAR (DIAL) system by increasing signal to noise ratios of measured pulse energies of the DIAL system, the method comprising the steps of:
   a) scanning the DIAL beam such that the DIAL beam is transmitted through a plurality of measurement points, the DIAL beam including an online laser beam and an offline laser beam transmitted collinearly;
   b) measuring a plurality of transmitted pulse energies of the online laser beam and a plurality of transmitted pulse energies of the offline laser beam corresponding to the plurality of measurement points;
   c) measuring a plurality of received pulse energies of the online laser beam and a plurality of received pulse energies of the offline laser beam corresponding to the plurality of measurement points;
   d) selecting one measurement point;
   e) selecting a region of interest (ROI) subset of measurement points within a ROI around the one selected measurement point;
   f) calculating, for the one selected measurement point:
      an average transmitted online pulse energy from the transmitted pulse energies of the online laser beam of the selected ROI subset of the measurement points;
      an average transmitted offline pulse energy from the transmitted pulse energies of the offline laser beam of the selected ROI subset of the measurement points;

an average received online pulse energy from the received pulse energies of the online laser beam of the selected ROI subset of the measurement points; and an average received offline pulse energy from the received pulse energies of the offline laser beam of the selected ROI subset of the measurement points; and g) calculating the CPL of the DIAL beam for the one selected measurement point using the average transmitted online pulse energy, the average transmitted offline pulse energy, the average received online pulse energy, and the average received offline pulse energy; and providing the calculated CPL to a user.

2. The method according to claim 1, wherein step (a) includes scanning the DIAL beam such that the plurality of measurement points through which the DIAL beam is transmitted are uniformly distributed.

3. The method according to claim 2, wherein the ROT around the one selected measurement point is a circle centered on the one selected measurement point and having a predetermined radius.

4. The method according to claim 3, wherein:
the plurality of measurement points are osculating; and
the predetermined radius of the ROT is approximately five times a beam radius of the DIAL beam.

5. The method according to claim 1, wherein step (a) includes scanning the DIAL beam such that a density of the plurality of measurement points through which the DIAL beam is transmitted varies.

6. The method according to claim 5, wherein:
the ROI around the one selected measurement point is a circle centered on the one selected measurement point; and
a radius of the circle is selected such that the ROI includes a predetermined number of measurement points.

7. The method according to claim 6, wherein the predetermined number of measurement points is about 25.

8. The method according to claim 1, wherein step (f) includes the steps of:

f1) calculating the average transmitted online pulse energy to be an unweighted average of the transmitted pulse energies of the online laser beam of the selected ROI subset of the measurement points;

f2) calculating the average transmitted offline pulse energy to be an unweighted average of the transmitted pulse energies of the offline laser beam of the selected ROT subset of the measurement points;

f3) calculating the average received online pulse energy to be an unweighted average of the received pulse energies of the online laser beam of the selected ROT subset of the measurement points; and f4) calculating the average received offline pulse energy to be an unweighted average of the received pulse energies of the offline laser beam of the selected ROT subset of the measurement points.

9. The method according to claim 1, wherein step (f) includes the steps of:

f1) calculating the average transmitted online pulse energy to be a weighted average of the transmitted pulse energies of the online laser beam of the selected ROT subset of the measurement points;

f2) calculating the average transmitted offline pulse energy to be a weighted average of the transmitted pulse energies of the offline laser beam of the selected ROT subset of the measurement points;

f3) calculating the average received online pulse energy to be a weighted average of the received pulse energies of the online laser beam of the selected ROT subset of the measurement points; and f4) calculating the average received offline pulse energy to be a weighted average of the received pulse energies of the offline laser beam of the selected ROI subset of the measurement points.

10. The method according to claim 9, wherein the weighted averages of steps (f1), (f2), (f3), and (f4) are calculated according to a circular Gaussian kernel weighting function.

11. The method according to claim 1, further comprising the step of:

h) repeating steps (d), (e), (f), (g) and (h) until all of the measurement points have been selected in step (d).

12. The method according to claim 11, further comprising the step of:

i) for each measurement point, determining whether the measurement point represents a plume point or a non-plume point using the corresponding CPL calculated in step (g).

13. The method according to claim 12, wherein step (i) includes, for each measurement point, the steps of:

i1) providing an average non-plume CPL, $\overline{CPL}$;

i2) calculating a standard deviation, $CPL_{sd}$, of each measurement point based on first order error propagation;

i3) calculating the CPL likelihood value of each measurement point, $$CPL\_LL = -\frac{1}{2}\ln(2\Pi) - \ln(CPL_{sd}) - \frac{1}{2}\left(\frac{cpl - \overline{CPL}}{CPL_{sd}}\right)^2,$$

where cpl is the corresponding CPL of the measurement point calculated in step (g); and i4) determining that the measurement point represents a non-plume point if the CPL likelihood value is less than a CPL threshold level, $$CPL\_LL_{threshold} = -\frac{1}{2}\ln(2\Pi) - \ln(CPL_{sd}) - \frac{1}{2}(T)^2,$$

where T is a threshold standard deviation level.

14. The method according to claim 13, wherein the average non-plume CPL is based on a non-plume local distribution of measurement points.

15. The method according to claim 13, wherein the average non-plume CPL is based on a training set of non-plume measurement points.

16. The method according to claim 12, wherein step (i) includes, for each measurement point, the steps of:

i1) providing an average non-plume CPL, $\overline{CPL}$;

i2) calculating a standard deviation, $CPL_{Sd}$, of each measurement point based on first order error propagation; and i3) determining that the measurement point represents a non-plume point when a Hooshmand decision rule (HDR) is met, the HDR being;

$$\left(\frac{cpl - \overline{CPL}}{CPL_{sd}}\right)^2 > (T)^2,$$

where cpl is the corresponding CPL of the measurement point calculated in step (g) and T is a threshold standard deviation level.

17. The method according to claim 16, wherein the average non-plume CPL is based on a non-plume local distribution of measurement points.

18. The method according to claim 16, wherein the average non-plume CPL is based on a training set of non-plume measurement points.

19. The method according to claim 12, further comprising the step of:
j) for each plume point determined in step (i), determining whether the plume point is a false plume point using the CPL's calculated in step (g).

20. The method according to claim 19, wherein step (j), for an $i^{th}$ plume point of the plume points determined in step (i), includes the steps of:
j1) selecting a $j^{th}$ measuring point from a nearest neighbor subset of the measurement points of the $i^{th}$ plume point, the nearest neighbor subset of the measurement points including the plume point and a predetermined number, K-1, of nearest neighbor measurement points;
j2) calculating an average CPL, $\overline{CPL_{ij}}$, of the CPL's of a local subset of measurement points around the $j^{th}$ measurement point;
j3) calculating a standard deviation, $(CPL_{sd})_j$, of each measurement point in the local subset based on first order error propagation;
j4) repeating steps (j1), (j2), and (j3) for j=1 to K;
j5) calculating the CPL likelihood value of the $i^{th}$ plume point, $$(CPL\_LL)_i = -\sum_{j=1}^{K} \ln(CPL_{sd})_j - \frac{1}{2}\sum_{j=1}^{K}\left[\frac{cpl_{ij} - \overline{CPL_j}}{(CPL_{sd})_j}\right]^2,$$

where $cpl_{ij}$ is the corresponding CPL of the $j^{th}$ measurement point calculated in step (g); and
j6) determining that the $i^{th}$ plume point represents a false plume point if the CPL likelihood value of the $i^{th}$ plume point is less than a CPL threshold level of the $i^{th}$ plume point, $$(CPL\_LL)_{Threshold} = -\sum_{j=1}^{K} \ln(CPL_{sd})_j - \frac{1}{2}KT^2,$$

where T is a threshold standard deviation level.

21. The method according to claim 20, wherein the predetermined number of nearest neighbors of the measurement point is 24.

22. An improved method for determining whether a measurement point, measured using a differential absorption LIDAR (DIAL) system, represents a plume point or a non-plume point, the method comprising the steps of:
a) determining concentration path lengths (CPL's) for a plurality of measurement points;
b) providing an average non-plume CPL, $\overline{CPL}$;
c) for each measurement point, calculating a standard deviation, $CPL_{sd}$, based on first order error propagation;
d) for each measurement point, calculating the CPL likelihood value, $$CPL\_LL = -\frac{1}{2}\ln(2\Pi) - \ln(CPL_{sd}) - \frac{1}{2}\left(\frac{cpl - \overline{CPL}}{CPL_{sd}}\right)^2,$$

where cpl is the corresponding CPL of the measurement point; and
e) for each measurement point, determining that the measurement point represents a non-plume point if the CPL likelihood value is less than a CPL threshold level, $$CPL\_LL_{threshold} = -\frac{1}{2}\ln(2\Pi) - \ln(CPL_{sd}) - \frac{1}{2}(T)^2,$$

where T is a threshold standard deviation level; and
f) providing the determination of the measurement point of step (e) to a user.

23. The method according to claim 22, wherein the average non-plume CPL is based on a non-plume local distribution of measurement points.

24. The method according to claim 22, wherein the average non-plume CPL is based on a training set of non-plume measurement points.

25. An improved method for determining whether a measurement point, measured using a differential absorption LIDAR (DIAL) system, represents a plume point or a non-plume point, the method comprising the steps of:
a) determining concentration path lengths (CPL's) for a plurality of measurement points;
b) providing an average non-plume CPL, $\overline{CPL}$;
c) for each measurement point, calculating a standard deviation, $CPL_{sd}$, based on first order error propagation; and
d) for each measurement point, determining that the measurement point represents a non-plume point when a Hooshmand decision rule (HDR) is met, the HDR being;

$$\left(\frac{cpl - \overline{CPL}}{CPL_{sd}}\right)^2 > (T)^2,$$

where cpl is the corresponding CPL of the measurement point calculated determined in step (a) and T is a threshold standard deviation level; and
e) providing the determination of the measurement point of step (d) to a user.

26. The method according to claim 25, wherein the average non-plume CPL is based on a non-plume local distribution of measurement points.

27. The method according to claim 25, wherein the average non-plume CPL is based on a training set of non-plume measurement points.

28. An improved method for discovering false plume points identified using a differential absorption LIDAR (DIAL) system, the method comprising the steps of:
 a) determining a concentration path length (CPL) for a plurality of measurement points;
 b) for each measurement point, determining whether the measurement point represents a plume point or a non-plume point using the corresponding CPL;
 c) selecting a $j^{th}$ measuring point from a nearest neighbor subset of the measurement points of one of the plume points determined in step (b), the nearest neighbor subset of the measurement points including the plume point and a predetermined number, K-1, of nearest neighbor measurement points;
 d) calculating an average CPL, $\overline{CPL_j}$, of the CPL's of a local subset of measurement points around the $j^{th}$ measurement point;
 e) calculating a standard deviation, $(CPL_{sd})_j$, of each measurement point in the local subset based on first order error propagation;
 f) repeating steps (c), (d), and (e) for j=1 to K;
 g) calculating the CPL joint likelihood value of the one plume point, $$(CPL\_LL) = -\sum_{j=1}^{K} \ln(CPL_{sd})_j - \frac{1}{2}\sum_{j=1}^{K}\left[\frac{cpl_j - \overline{CPL_j}}{(CPL_{sd})_j}\right]^2,$$

where $cpl_j$ is the corresponding CPL of the $j^{th}$ measurement point;
 h) determining that the one plume point represents a false plume point if the CPL joint likelihood value of the one plume point is less than a CPL threshold level of the one plume point, $$(CPL\_LL)_{Threshold} = -\sum_{j=1}^{K} \ln(CPL_{sd})_j - \frac{1}{2}KT^2,$$

where T is a threshold standard deviation level;
 i) repeating steps (c), (d), (e), (f), (g), and (h) for each plume point determined in step (b); and
 j) providing the determination of step (b) to a user.

29. The method according to claim 28, wherein the predetermined number of nearest neighbors of the measurement point is about 24.

30. An improved method for classifying uncertain labeled points of a plurality of measurement points identified using a differential absorption LIDAR (DIAL) system, the method comprising the steps of:
 a) determining a concentration path length (CPL) for the plurality of measurement points;
 b) for each measurement point, determining whether the measurement point represents a plume point, a non-plume point, or an uncertain labeled point using the corresponding CPL;
 c) selecting a $j^{th}$ measuring point from a nearest neighbor subset of the measurement points of one of the uncertain labeled points determined in step (b), the nearest neighbor subset of the measurement points including the uncertain labeled point and a predetermined number, K-1, of nearest neighbor measurement points;
 d) calculating an average CPL, $\overline{CPL_j}$, of the CPL's of a local subset of measurement points around the $j^{th}$ measurement point;
 e) calculating a standard deviation, $(CPL_{sd})_j$, of each measurement point in the local subset based on first order error propagation;
 f) repeating steps (c), (d), and (e) for j=1 to K;
 g) calculating the CPL joint likelihood value of the one uncertain labeled point, $$(CPL\_LL) = -\sum_{j=1}^{K} \ln(CPL_{sd})_j - \frac{1}{2}\sum_{j=1}^{K}\left[\frac{cpl_j - \overline{CPL_j}}{(CPL_{sd})_j}\right]^2,$$

where $cpl_j$ is the corresponding CPL of the $j^{th}$ measurement point;
 h) determining that the one uncertain labeled point represents a non-plume point if the CPL joint likelihood value of the one uncertain labeled point is greater than or equal to a CPL threshold level of the one uncertain labeled point, $$(CPL\_LL)_{Threshold} = -\sum_{j=1}^{K} \ln(CPL_{sd})_j - \frac{1}{2}KT^2,$$

and that the one uncertain labeled point represents a plume point if the CPL joint likelihood value of the one uncertain labeled point is less than the CPL threshold level of the one uncertain labeled point, where T is a threshold standard deviation level;
 i) repeating steps (c), (d), (e), (f), (g), and (h) for each uncertain labeled point determined in step (b), and
 j) providing the determination of step (b) to a user.

31. The method according to claim 30, wherein the predetermined number of nearest neighbors of the measurement point is about 24.

32. A system for calculating and providing concentration path length (CPL) to a user in a differential absorption LIDAR (DIAL) system comprising:
 a transmitter for transmitting a DIAL beam including online pulsed laser energies and an offline pulsed laser energies,
 a scanner for scanning the DIAL beam such that the DIAL beam is transmitted toward a plurality of measurement points,
 a receiver for receiving a plurality of online and offline pulsed laser energies corresponding to the plurality of measurement points, and
 a processor configured to (a) select at least one measurement point and a region of interest (ROI) around the one measurement point, and (b) calculate for the one selected measurement point (i) an average transmitted online pulsed energy in the selected ROI, (ii) an average transmitted offline pulsed energy in the selected ROI, (iii) an average received online pulsed energy in the selected ROI, and (iv) an average received offline pulsed energy in the selected ROI,
 wherein the processor is configured to calculate, and provide to the user, the CPL for the at least one selected measurement point using the average transmitted online pulsed energy, the average transmitted offline pulsed energy, the average received online pulsed energy, and the average received offline pulsed energy.

* * * * *